US011274310B2

(12) United States Patent
De Bruijn et al.

(10) Patent No.: US 11,274,310 B2
(45) Date of Patent: *Mar. 15, 2022

(54) YEAST CELLS FOR GLYCEROL FREE ETHANOL PRODUCTION

(71) Applicant: DSM IP ASSETS B.V., Heerlen (NL)

(72) Inventors: Hans Marinus Charles Johannes De Bruijn, Echt (NL); Paulus Petrus De Waal, Echt (NL); Ingrid Maria Vugt-Van Lutz, Echt (NL)

(73) Assignee: DSM IP ASSETS B.V., Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/643,936

(22) PCT Filed: Sep. 25, 2018

(86) PCT No.: PCT/EP2018/075959
§ 371 (c)(1),
(2) Date: Mar. 3, 2020

(87) PCT Pub. No.: WO2019/063543
PCT Pub. Date: Apr. 4, 2019

(65) Prior Publication Data
US 2020/0407733 A1 Dec. 31, 2020

(30) Foreign Application Priority Data

Sep. 29, 2017 (EP) .................................. 1719315
Aug. 28, 2018 (EP) .................................. 18191191

(51) Int. Cl.
C12N 15/81 (2006.01)
C12N 9/04 (2006.01)
C12N 9/12 (2006.01)
C12N 9/34 (2006.01)
C12N 9/88 (2006.01)
C12P 7/06 (2006.01)

(52) U.S. Cl.
CPC ........... C12N 15/81 (2013.01); C12N 9/0006 (2013.01); C12N 9/1205 (2013.01); C12N 9/2428 (2013.01); C12N 9/88 (2013.01); C12P 7/06 (2013.01); C12Y 101/01006 (2013.01); C12Y 207/01019 (2013.01); C12Y 302/01003 (2013.01); C12Y 401/01039 (2013.01)

(58) Field of Classification Search
None
See application file for complete search history.

(56) References Cited

U.S. PATENT DOCUMENTS

2011/0136195 A1* 6/2011 Richards .................. C12N 1/18
435/161
2012/0276593 A1 11/2012 Li et al.
2015/0176032 A1* 6/2015 De Bont .................. C12P 7/08
435/161
2015/0353942 A1* 12/2015 Van Maris ................ C12P 7/62
435/106
2016/0194669 A1* 7/2016 Argyros ......... C12Y 101/01008
435/161

FOREIGN PATENT DOCUMENTS

| EP | 0260404 A2 | 3/1988 |
| EP | 2277989 A1 | 1/2011 |
| FR | 3040395 A1 | 3/2017 |
| WO | 2005/113785 A2 | 12/2005 |
| WO | 2011/068803 A1 | 6/2011 |
| WO | 2011/100161 A1 | 8/2011 |
| WO | 2012/064351 A1 | 5/2012 |
| WO | 2015/143317 A1 | 9/2015 |
| WO | 2016/062875 A2 | 4/2016 |
| WO | 2016/127083 A1 | 8/2016 |
| WO | 2016/160584 A1 | 10/2016 |
| WO | 2017/112631 A1 | 6/2017 |
| WO | WO-2018114762 A1 * | 6/2018 ..... C12Y 101/01006 |

OTHER PUBLICATIONS

Chica et al. CurrOpin Biotechnol. Aug. 2005;16(4):378-84. (Year: 2005).*
Singh et al. Curr Protein Pept Sci. 2017, 18, 1-11 (Year: 2017).*
Accession M2RLN3. May 1, 2013. (Year: 2013).*
Gibson et al. FEMS Microbiol Rev. Sep. 2007;31(5):535-69. (Year: 2007).*
Viktor et al. Biotechnol Biofuels. Nov. 29, 2013;6(1):167. (Year: 2013).*
Klein et al. Metab Eng. Nov. 2016;38:464-472. (Year: 2016).*
Accession XP_007380558. Mar. 27, 2014 (Year: 2014).*
Alignment of Accession XP_007380558 to SEQ ID No. 17 (Year: 2014).*
Sambrook et al. Molecular cloning A Laboratory Manual, 2nd edition, Cold Spring Harbor, N.Y. 1989, pp. 8.46-8.52 and pp. 11.2-11.19. (Year: 1989).*
Cole, Georgette E. et al., "Stable Expression of Aspergillus Awamori Glucoamylase in Distiller's Yeast", Bio/Technology, Apr. 1988, pp. 417-421, vol. 6.
Gorgens, Johann F. et al., "Engineering Saccharomyces cerevisiae for direct conversion of raw, uncooked or granular starch to ethanol", Critical Reviews in Biotechnology, 2015, pp. 369-391, vol. 35, No. 3.
Lee, Dae-Hee et al., "Ethanol Fermentation of Corn Starch by a Recombinant Saccharomyces cerevisiae Having Glucoamylase and α-Arylase Activities", The Journal of Food Science and Nutrition, 2001, pp. 206-210, vol. 6, No. 4.
International Search Report of International Patent Application No. PCT/EP2018/075959 dated Oct. 23, 2018.

* cited by examiner

Primary Examiner — Christian L Fronda
(74) Attorney, Agent, or Firm — McBee Moore & Vanik IP, LLC; Susan McBee; Chester Moore

(57) ABSTRACT

The invention relates to a recombinant yeast comprising a nucleotide sequence allowing the expression of a glucoamylasey (EC 3.2.1.20 or 3.2.1.3). This cell can be used for the production of ethanol and advantageously produces little or no glycerol.

16 Claims, No Drawings

Specification includes a Sequence Listing.

SEQUENCE LISTING

<160> NUMBER OF SEQ ID NOS: 53

<210> SEQ ID NO 1
<211> LENGTH: 365
<212> TYPE: PRT
<213> ORGANISM: Klebsiella pneumoniae
<220> FEATURE:
<221> NAME/KEY: MISC_FEATURE
<222> LOCATION: (1)..(365)
<223> OTHER INFORMATION: K. pneumoniae glycerol dehydrogenase
      (Kpne_gldA) amino acid sequence

<400> SEQUENCE: 1

Met Leu Lys Val Ile Gln Ser Pro Ala Lys Tyr Leu Gln Gly Pro Asp
1               5                   10                  15

Ala Ala Val Leu Phe Gly Gln Tyr Ala Lys Asn Leu Ala Glu Ser Phe
            20                  25                  30

```
Phe Val Ile Ala Asp Asp Phe Met Lys Leu Ala Gly Glu Lys Val
            35                  40                  45

Val Asn Gly Leu Gln Ser His Asp Ile Arg Cys His Ala Glu Arg Phe
 50                  55                  60

Asn Gly Glu Cys Ser His Ala Glu Ile Asn Arg Leu Met Ala Ile Leu
 65                  70                  75                  80

Gln Lys Gln Gly Cys Arg Gly Val Val Gly Ile Gly Gly Lys Thr
            85                  90                  95

Leu Asp Thr Ala Lys Ala Ile Gly Tyr Tyr Gln Lys Leu Pro Val Val
            100                 105                 110

Val Ile Pro Thr Ile Ala Ser Thr Asp Ala Pro Thr Ser Ala Leu Ser
            115                 120                 125

Val Ile Tyr Thr Glu Ala Gly Glu Phe Glu Tyr Leu Ile Tyr Pro
            130                 135                 140

Lys Asn Pro Asp Met Val Val Met Asp Thr Ala Ile Ile Ala Lys Ala
145                 150                 155                 160

Pro Val Arg Leu Leu Val Ser Gly Met Gly Asp Ala Leu Ser Thr Trp
            165                 170                 175

Phe Glu Ala Lys Ala Cys Tyr Asp Ala Arg Ala Thr Ser Met Ala Gly
            180                 185                 190

Gly Gln Ser Thr Glu Ala Ala Leu Ser Leu Ala Arg Leu Cys Tyr Asp
            195                 200                 205

Thr Leu Leu Ala Glu Gly Glu Lys Ala Arg Leu Ala Ala Gln Ala Gly
            210                 215                 220

Val Val Thr Glu Ala Leu Glu Arg Ile Ile Glu Ala Asn Thr Tyr Leu
225                 230                 235                 240

Ser Gly Ile Gly Phe Glu Ser Ser Gly Leu Ala Ala His Ala Ile
            245                 250                 255

His Asn Gly Phe Thr Ile Leu Glu Glu Cys His His Leu Tyr His Gly
            260                 265                 270

Glu Lys Val Ala Phe Gly Thr Leu Ala Gln Leu Val Leu Gln Asn Ser
            275                 280                 285

Pro Met Asp Glu Ile Glu Thr Val Leu Gly Phe Cys Gln Arg Val Gly
            290                 295                 300

Leu Pro Val Thr Leu Ala Gln Met Gly Val Lys Glu Gly Ile Asp Ala
305                 310                 315                 320

Lys Ile Ala Ala Val Ala Lys Ala Thr Cys Ala Glu Gly Glu Thr Ile
            325                 330                 335

His Asn Met Pro Phe Ala Val Thr Pro Glu Ser Val His Ala Ala Ile
            340                 345                 350

Leu Thr Ala Asp Leu Leu Gly Gln Gln Trp Leu Ala Arg
            355                 360                 365

<210> SEQ ID NO 2
<211> LENGTH: 367
<212> TYPE: PRT
<213> ORGANISM: Enterococcus aerogenes
<220> FEATURE:
<221> NAME/KEY: MISC_FEATURE
<222> LOCATION: (1)..(367)
<223> OTHER INFORMATION: E. aerogenes glycerol dehydrogenase (Eaer_gldA)
      amino acid sequence

<400> SEQUENCE: 2

Met Asp Arg Ile Ile Gln Ser Pro Gly Lys Tyr Ile Gln Gly Ala Gly
 1               5                   10                  15
```

Ala Ile Lys Arg Leu Gly Glu Tyr Leu Lys Pro Leu Ala Glu Arg Trp
            20                  25                  30

Leu Ile Ile Gly Asp Lys Phe Val Leu Gly Phe Ala Glu Glu Gln Leu
        35                  40                  45

Arg Thr Ser Leu Gly Gly Ala Gly Leu Val Ala Glu Ile Ala Pro Phe
    50                  55                  60

Gly Gly Glu Cys Ser Gln Asn Glu Ile Asn Arg Leu Arg Asp Ile Ala
65                  70                  75                  80

Ser Ser Ala Gln Cys His Ala Val Leu Gly Ile Gly Gly Lys Thr
                85                  90                  95

Leu Asp Thr Ala Lys Ala Leu Ala His Tyr Met His Leu Pro Val Val
                100                 105                 110

Val Ala Pro Thr Ile Ala Ser Thr Asp Ala Pro Cys Ser Ala Leu Ser
            115                 120                 125

Val Ile Tyr Thr Asp Gly Glu Phe Glu Ser Tyr Leu Met Leu Pro
130                 135                 140

His Asn Pro Asn Met Val Val Asp Thr Gln Ile Val Ala Ala Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
                180                 185                 190

Gly Lys Cys Thr Gln Ala Ala Leu Ala Leu Glu Leu Cys Tyr Asn
            195                 200                 205

Thr Leu Val Glu Glu Gly Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala His Ala Ile
                245                 250                 255

His Asn Gly Leu Thr Ala Ile Pro Asp Ala His His Phe Tyr His Gly
                260                 265                 270

Glu Lys Val Ala Phe Gly Thr Leu Thr Gln Leu Val Leu Glu Asn Ala
            275                 280                 285

Pro Val Glu Glu Ile Glu Thr Ala Ala Ala Leu Cys His Ser Val Gly
290                 295                 300

Leu Pro Ile Thr Leu Ala Gln Leu Asp Ile Lys Gly Asp Ile Pro Ala
305                 310                 315                 320

Lys Met Arg Thr Val Ala Glu Ala Ala Cys Ala Glu Gly Glu Thr Ile
                325                 330                 335

His Asn Met Pro Gly Gly Ala Cys Ala Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 3
<211> LENGTH: 364
<212> TYPE: PRT
<213> ORGANISM: Yersinia aldovae
<220> FEATURE:
<221> NAME/KEY: MISC_FEATURE
<222> LOCATION: (1)..(364)
<223> OTHER INFORMATION: Y. aldovae glycerol dehydrogenase (Eaer_gldA)
      amino acid sequence

<400> SEQUENCE: 3

```
Met Leu Lys Val Ile Gln Ser Pro Ser Lys Tyr Ile Gln Gly Ala Asn
1               5                   10                  15

Ala Leu Gln Ser Ile Gly Glu Phe Ala Lys Leu Leu Ala Asn Asn Tyr
            20                  25                  30

Phe Ile Ile Ala Asp Asp Phe Val Met Lys Leu Thr Ala Asp Thr Val
        35                  40                  45

Gly Thr Ser Leu Gln Thr Cys Glu Leu Lys Ser His Phe Ser Arg Phe
50                  55                  60

Asn Gly Glu Cys Ser Arg Gln Glu Ile Glu Arg Leu Thr Val Glu Leu
65                  70                  75                  80

Lys Lys Tyr Gly Cys Asn Gly Val Ile Gly Ile Gly Gly Lys Thr
                85                  90                  95

Leu Asp Thr Ala Lys Ala Ile Ala His Tyr Gln His Ile Pro Val Val
            100                 105                 110

Val Val Pro Thr Ile Ala Ser Thr Asp Ala Pro Thr Ser Ala Leu Ser
        115                 120                 125

Val Ile Tyr Thr Glu Gln Gly Glu Phe Ala Glu Tyr Leu Ile Tyr Pro
    130                 135                 140

Lys Asn Pro Asp Ile Val Leu Met Asp Thr Thr Ile Ala Lys Ala
145                 150                 155                 160

Pro Val Arg Leu Leu Val Ala Gly Met Gly Asp Ala Leu Ser Thr Tyr
                165                 170                 175

Phe Glu Ala Gln Ala Cys Phe Asp Ala Lys Ala Ile Ser Met Ala Gly
            180                 185                 190

Gly Ala Ser Thr Leu Ala Ala Ile Thr Leu Ala Arg Leu Cys Tyr Glu
        195                 200                 205

Thr Leu Leu Ala Glu Gly Tyr Lys Ala Lys Leu Ala Val Glu Ala Gly
    210                 215                 220

Val Val Thr Glu Ala Val Glu Arg Ile Ile Glu Ala Asn Thr Tyr Leu
225                 230                 235                 240

Ser Gly Ile Gly Phe Glu Ser Ser Gly Leu Ala Ala Ala His Ala Ile
                245                 250                 255

His Asn Gly Phe Thr Val Leu Glu Glu Cys His His Leu Tyr His Gly
            260                 265                 270

Glu Lys Val Ala Phe Gly Thr Leu Thr Gln Leu Val Leu Gln Asn Ser
        275                 280                 285

Ser Met Glu Glu Ile Glu Thr Val Leu Ser Phe Cys Gln Gln Leu Gly
    290                 295                 300

Leu Pro Ile Thr Leu Ala Glu Met Gly Val Thr Gln Asp Leu Glu Cys
305                 310                 315                 320

Lys Ile Arg Ala Val Ala Gln Ala Ser Cys Ala Glu Gly Glu Thr Ile
                325                 330                 335

His Asn Met Pro Phe Lys Val Thr Ala Asp Ser Val Tyr Ala Ala Ile
            340                 345                 350

Ile Val Ala Asp Arg Leu Gly Gln Ala Phe Leu Asn
        355                 360

<210> SEQ ID NO 4
<211> LENGTH: 572
<212> TYPE: PRT
<213> ORGANISM: Klebsiella pneumoniae
<220> FEATURE:
<221> NAME/KEY: MISC_FEATURE
<222> LOCATION: (1)..(572)
<223> OTHER INFORMATION: K. pneumoniae dihydroxyacetone kinase
```

(Kpne_dhaK) amino acid sequence

<400> SEQUENCE: 4

```
Met Thr Thr Lys Gln Phe Gln Phe Asp Ser Asp Pro Leu Asn Ser Ala
1               5                   10                  15
Leu Ala Ala Thr Ala Glu Ala Ser Gly Leu Ala Tyr Leu Pro Lys Ser
            20                  25                  30
Lys Val Ile Tyr Tyr Pro Leu Thr Asn Asp Lys Val Thr Leu Ile Ser
        35                  40                  45
Gly Gly Gly Ala Gly His Glu Pro Ala Gln Thr Gly Phe Val Gly Pro
50                  55                  60
Gly Leu Leu Asp Ala Ala Val Ser Gly Gln Ile Phe Ala Ser Pro Ser
65                  70                  75                  80
Thr Lys Gln Ile Ile Ala Gly Val Asn Ala Val Lys Ser Gln Arg Gly
                85                  90                  95
Ser Ile Ile Ile Val Met Asn Tyr Thr Gly Asp Val Ile His Phe Gly
            100                 105                 110
Met Ala Ala Glu Gln Leu Arg Ser Arg Tyr Asp Tyr His Ala Glu Leu
        115                 120                 125
Val Ser Ile Gly Asp Asp Ile Ser Val Asn Lys Lys Ala Gly Arg Arg
130                 135                 140
Gly Leu Ala Gly Thr Val Leu Val His Lys Ile Ala Gly His Leu Ala
145                 150                 155                 160
Arg Asp Gly Trp Asp Val Gly Val Leu Ala Glu Ala Leu Arg Thr Thr
                165                 170                 175
Ala Ala Asn Leu Ala Thr Val Ala Ala Ser Leu Glu His Cys Thr Val
            180                 185                 190
Pro Gly Arg Lys Phe Glu Thr Glu Leu Ala Ala Asp Glu Met Glu Ile
        195                 200                 205
Gly Met Gly Ile His Asn Glu Pro Gly Val Lys Thr Ile Lys Ile Gly
210                 215                 220
Lys Val Glu Ser Leu Leu Asp Glu Leu Val Asp Lys Phe Glu Pro Ser
225                 230                 235                 240
Lys Gln Asp Phe Val Pro Phe Asn Lys Gly Asp Glu Val Val Leu Leu
                245                 250                 255
Val Asn Ser Leu Gly Gly Val Ser Ser Leu Glu Leu His Ala Ile Ala
            260                 265                 270
Asn Ile Ala Gln Thr Lys Phe Glu Lys Val Leu Gly Val Lys Thr Val
        275                 280                 285
Arg Leu Ile Val Gly Asn Phe Met Ala Ala Phe Asn Gly Pro Gly Phe
290                 295                 300
Ser Leu Thr Leu Leu Asn Val Thr Thr Thr Ala Lys Lys Gly Asn Phe
305                 310                 315                 320
Asp Val Leu Gly Ala Leu Asp Ala Pro Val Ser Thr Ala Ala Trp Pro
                325                 330                 335
Ser Leu Gln Gln Lys Asp Lys Pro Ala Asn Gly Val Gln Glu Glu
            340                 345                 350
Lys Glu Thr Asp Ser Asp Lys Pro Ala Glu Pro Thr Gly Ile Lys Ala
        355                 360                 365
Asp Gly Lys Leu Phe Lys Ala Met Ile Glu Ser Ala Val Asp Asp Leu
370                 375                 380
Lys Lys Glu Glu Pro Gln Ile Thr Lys Tyr Asp Thr Ile Ala Gly Asp
385                 390                 395                 400
```

```
Gly Asp Cys Gly Glu Thr Leu Leu Ala Gly Asp Gly Ile Leu Asp
            405                 410                 415

Ala Ile Lys Asn Lys Lys Ile Asp Leu Asp Asp Ala Ala Gly Val Ala
        420                 425                 430

Asp Ile Ser His Ile Val Glu Asn Ser Met Gly Gly Thr Ser Gly Gly
        435                 440                 445

Leu Tyr Ser Ile Phe Phe Ser Gly Leu Val Val Gly Ile Lys Glu Thr
    450                 455                 460

Lys Ala Lys Glu Leu Ser Val Asp Val Phe Ala Lys Ala Cys Glu Thr
465                 470                 475                 480

Ala Leu Glu Thr Leu Ser Lys Tyr Thr Gln Ala Arg Val Gly Asp Arg
                485                 490                 495

Thr Leu Met Asp Ala Leu Val Pro Phe Val Glu Thr Leu Ser Lys Thr
                500                 505                 510

Lys Asp Phe Ala Lys Ala Val Glu Ala Ala Arg Lys Gly Ala Asp Glu
            515                 520                 525

Thr Ser Lys Leu Pro Ala Asn Phe Gly Arg Ala Ser Tyr Val Asn Glu
        530                 535                 540

Glu Gly Leu Glu Asn Ile Pro Asp Pro Gly Ala Leu Gly Leu Ala Val
545                 550                 555                 560

Ile Phe Glu Gly Leu Leu Lys Ala Trp Glu Lys Lys
                565                 570

<210> SEQ ID NO 5
<211> LENGTH: 580
<212> TYPE: PRT
<213> ORGANISM: Yarrowia lipolytica
<220> FEATURE:
<221> NAME/KEY: MISC_FEATURE
<222> LOCATION: (1)..(580)
<223> OTHER INFORMATION: Y. lipolytica dihydroxyacetone kinase
      (Ylip_DAK1) amino acid sequence

<400> SEQUENCE: 5

Met Asp Lys His Phe Ile Asn Asp Pro Glu Val Leu Val Leu Asp Gly
1               5                   10                  15

Leu Lys Ser Leu Ala Asp Met Asn Lys Thr Leu Thr Val His Glu Glu
            20                  25                  30

Gly Lys Phe Ile Tyr Phe His Asp Tyr Asn Lys Lys Asn Val Ser Val
        35                  40                  45

Ile Ser Gly Gly Gly Ala Gly His Glu Pro Thr His Ser Ser Phe Val
    50                  55                  60

Gly Lys Gly Met Leu Thr Ala Ala Val Ser Gly Ser Ile Phe Ala Ser
65                  70                  75                  80

Pro Ser Ser Lys Gln Ile Tyr Thr Gly Ile Lys Gln Val Glu Ser Glu
                85                  90                  95

Ala Gly Thr Leu Val Ile Cys Lys Asn Tyr Thr Gly Asp Ile Leu His
            100                 105                 110

Phe Gly Met Ala Leu Glu Lys Gln Arg Thr Ala Gly Lys Lys Ala Glu
        115                 120                 125

Leu Ile Ala Val Ala Asp Asp Val Ser Val Gly Arg Lys Lys Ser Gly
    130                 135                 140

Lys Val Gly Arg Arg Gly Leu Ser Gly Thr Val Leu Val His Lys Ile
145                 150                 155                 160

Ala Gly Ala Ala Ala Ala Arg Gly Leu Pro Leu Glu Ala Val Thr Thr
                165                 170                 175
```

```
Ile Ala Lys Ala Ala Ile Asp Asn Leu Val Ser Ile Gly Ala Ser Leu
            180                 185                 190
Ala His Val His Val Pro Gly His Glu Pro Ile Ala Lys Glu Asp Glu
        195                 200                 205
Met Lys His Asp Glu Met Glu Leu Gly Met Gly Ile His Asn Glu Pro
    210                 215                 220
Gly Cys Lys Arg Ile Ser Pro Ile Pro Ser Ile Asp Asp Leu Ile Ala
225                 230                 235                 240
Gln Met Leu Lys Gln Met Leu Asp Gln Ser Asp Lys Asp Arg Ala Tyr
                245                 250                 255
Val Lys Ile Glu Gly Asp Asp Glu Val Val Leu Leu Met Asn Asn Leu
            260                 265                 270
Gly Gly Leu Ser Met Leu Glu Phe Ser Ala Ile Ser His Lys Val Lys
        275                 280                 285
Glu Ala Leu Ala Lys Glu Tyr Lys Ile Asn Pro Val Arg Ile Phe Ala
    290                 295                 300
Gly Pro Phe Thr Thr Ser Leu Asn Gly Leu Gly Phe Gly Ile Thr Leu
305                 310                 315                 320
Leu Arg Thr Thr Asp Arg Val Lys Val Glu Gly Glu Tyr Ser Leu
                325                 330                 335
Val Asp Leu Ile Asp Gln Pro Val Glu Ala Ile Gly Trp Pro Leu Cys
            340                 345                 350
Gln Pro Ser Asp Leu Lys Ser Lys Asn Lys Ile Gly Asn Val Ser Ile
        355                 360                 365
Glu Glu Gly Gln Lys Asp Val Lys Ser Pro Val Thr Val Asp Lys Glu
    370                 375                 380
Lys Val Arg Gln Ala Ile Val Asn Ser Met Glu Asn Leu Ile Lys Ala
385                 390                 395                 400
Glu Pro Lys Ile Thr Lys Phe Asp Thr Met Ala Gly Asp Gly Asp Cys
                405                 410                 415
Gly Thr Thr Leu Lys Arg Gly Ala Glu Gly Val Leu Lys Phe Val Lys
            420                 425                 430
Ser Asp Lys Phe Ser Asp Asp Pro Ile Arg Ile Val Arg Asp Ile Ala
        435                 440                 445
Asp Val Ile Glu Asp Asn Met Asp Gly Thr Ser Gly Ala Leu Tyr Ala
    450                 455                 460
Ile Phe Phe His Gly Phe Ala Lys Gly Met Lys Asp Thr Leu Glu Lys
465                 470                 475                 480
Ser Lys Asp Ile Ser Ser Lys Thr Trp Ala Ala Gly Leu Lys Val Ala
                485                 490                 495
Leu Asp Thr Leu Phe Lys Tyr Thr Pro Ala Arg Pro Gly Asp Ser Thr
            500                 505                 510
Met Cys Asp Ala Leu Val Pro Phe Val Glu Thr Phe Val Lys Thr Asn
        515                 520                 525
Asp Leu Asn Ala Ala Val Glu Glu Ala Arg Lys Gly Ala Asp Ala Thr
    530                 535                 540
Ala Asp Met Gln Ala Lys Leu Gly Arg Ala Val Tyr Val Gly Asp Asp
545                 550                 555                 560
Val Lys Val Pro Asp Ala Gly Ala Leu Gly Val Ala Ile Val Glu
                565                 570                 575
Gly Phe Thr Lys
            580
```

```
<210> SEQ ID NO 6
<211> LENGTH: 580
<212> TYPE: PRT
<213> ORGANISM: Schizosaccharomyces pombe
<220> FEATURE:
<221> NAME/KEY: MISC_FEATURE
<222> LOCATION: (1)..(580)
<223> OTHER INFORMATION: S. pombe dihydroxyacetone kinase (Spom_DAK1)
      amino acid sequence

<400> SEQUENCE: 6
```

| | | | | | | | | | | | | | | |
|---|---|---|---|---|---|---|---|---|---|---|---|---|---|---|
| Met | Asp | Lys | His | Phe | Ile | Asn | Asp | Pro | Glu | Val | Leu | Val | Leu | Asp | Gly |
| 1 | | | | 5 | | | | | 10 | | | | | 15 | |
| Leu | Lys | Ser | Leu | Ala | Asp | Met | Asn | Lys | Thr | Leu | Thr | Val | His | Glu | Glu |
| | | | 20 | | | | | 25 | | | | | 30 | | |
| Gly | Lys | Phe | Ile | Tyr | Phe | His | Asp | Tyr | Asn | Lys | Lys | Asn | Val | Ser | Val |
| | | | 35 | | | | 40 | | | | | 45 | | | |
| Ile | Ser | Gly | Gly | Gly | Ala | Gly | His | Glu | Pro | Thr | His | Ser | Ser | Phe | Val |
| | 50 | | | | | 55 | | | | | 60 | | | | |
| Gly | Lys | Gly | Met | Leu | Thr | Ala | Ala | Val | Ser | Gly | Ser | Ile | Phe | Ala | Ser |
| 65 | | | | | 70 | | | | | 75 | | | | | 80 |
| Pro | Ser | Ser | Lys | Gln | Ile | Tyr | Thr | Gly | Ile | Lys | Gln | Val | Glu | Ser | Glu |
| | | | | 85 | | | | | 90 | | | | | 95 | |
| Ala | Gly | Thr | Leu | Val | Ile | Cys | Lys | Asn | Tyr | Thr | Gly | Asp | Ile | Leu | His |
| | | | 100 | | | | | 105 | | | | | 110 | | |
| Phe | Gly | Met | Ala | Leu | Glu | Lys | Gln | Arg | Thr | Ala | Gly | Lys | Lys | Ala | Glu |
| | | | 115 | | | | | 120 | | | | | 125 | | |
| Leu | Ile | Ala | Val | Ala | Asp | Asp | Val | Ser | Val | Gly | Arg | Lys | Lys | Ser | Gly |
| | 130 | | | | | 135 | | | | | 140 | | | | |
| Lys | Val | Gly | Arg | Arg | Gly | Leu | Ser | Gly | Thr | Val | Leu | Val | His | Lys | Ile |
| 145 | | | | | 150 | | | | | 155 | | | | | 160 |
| Ala | Gly | Ala | Ala | Ala | Ala | Arg | Gly | Leu | Pro | Leu | Glu | Ala | Val | Thr | Thr |
| | | | | 165 | | | | | 170 | | | | | 175 | |
| Ile | Ala | Lys | Ala | Ala | Ile | Asp | Asn | Leu | Val | Ser | Ile | Gly | Ala | Ser | Leu |
| | | | 180 | | | | | 185 | | | | | 190 | | |
| Ala | His | Val | His | Val | Pro | Gly | His | Glu | Pro | Ile | Ala | Lys | Glu | Asp | Glu |
| | | | 195 | | | | | 200 | | | | | 205 | | |
| Met | Lys | His | Asp | Glu | Met | Glu | Leu | Gly | Met | Gly | Ile | His | Asn | Glu | Pro |
| | 210 | | | | | 215 | | | | | 220 | | | | |
| Gly | Cys | Lys | Arg | Ile | Ser | Pro | Ile | Pro | Ser | Ile | Asp | Asp | Leu | Ile | Ala |
| 225 | | | | | 230 | | | | | 235 | | | | | 240 |
| Gln | Met | Leu | Lys | Gln | Met | Leu | Asp | Gln | Ser | Asp | Lys | Asp | Arg | Ala | Tyr |
| | | | | 245 | | | | | 250 | | | | | 255 | |
| Val | Lys | Ile | Glu | Gly | Asp | Asp | Glu | Val | Val | Leu | Leu | Met | Asn | Asn | Leu |
| | | | 260 | | | | | 265 | | | | | 270 | | |
| Gly | Gly | Leu | Ser | Met | Leu | Glu | Phe | Ser | Ala | Ile | Ser | His | Lys | Val | Lys |
| | | | 275 | | | | | 280 | | | | | 285 | | |
| Glu | Ala | Leu | Ala | Lys | Glu | Tyr | Lys | Ile | Asn | Pro | Val | Arg | Ile | Phe | Ala |
| | 290 | | | | | 295 | | | | | 300 | | | | |
| Gly | Pro | Phe | Thr | Thr | Ser | Leu | Asn | Gly | Leu | Gly | Phe | Gly | Ile | Thr | Leu |
| 305 | | | | | 310 | | | | | 315 | | | | | 320 |
| Leu | Arg | Thr | Thr | Asp | Arg | Val | Lys | Val | Glu | Gly | Glu | Glu | Tyr | Ser | Leu |
| | | | | 325 | | | | | 330 | | | | | 335 | |
| Val | Asp | Leu | Ile | Asp | Gln | Pro | Val | Glu | Ala | Ile | Gly | Trp | Pro | Leu | Cys |
| | | | 340 | | | | | 345 | | | | | 350 | | |
| Gln | Pro | Ser | Asp | Leu | Lys | Ser | Lys | Asn | Lys | Ile | Gly | Asn | Val | Ser | Ile |

```
            355                 360                 365
Glu Glu Gly Gln Lys Asp Val Lys Ser Pro Val Thr Val Asp Lys Glu
370                 375                 380

Lys Val Arg Gln Ala Ile Val Asn Ser Met Glu Asn Leu Ile Lys Ala
385                 390                 395                 400

Glu Pro Lys Ile Thr Lys Phe Asp Thr Met Ala Gly Asp Gly Asp Cys
                    405                 410                 415

Gly Thr Thr Leu Lys Arg Gly Ala Glu Gly Val Leu Lys Phe Val Lys
                420                 425                 430

Ser Asp Lys Phe Ser Asp Pro Ile Arg Ile Val Arg Asp Ile Ala
                435                 440                 445

Asp Val Ile Glu Asp Asn Met Asp Gly Thr Ser Gly Ala Leu Tyr Ala
        450                 455                 460

Ile Phe Phe His Gly Phe Ala Lys Gly Met Lys Asp Thr Leu Glu Lys
465                 470                 475                 480

Ser Lys Asp Ile Ser Ser Lys Thr Trp Ala Ala Gly Leu Lys Val Ala
                485                 490                 495

Leu Asp Thr Leu Phe Lys Tyr Thr Pro Ala Arg Pro Gly Asp Ser Thr
                500                 505                 510

Met Cys Asp Ala Leu Val Pro Phe Val Glu Thr Phe Val Lys Thr Asn
                515                 520                 525

Asp Leu Asn Ala Ala Val Glu Glu Ala Arg Lys Gly Ala Asp Ala Thr
        530                 535                 540

Ala Asp Met Gln Ala Lys Leu Gly Arg Ala Val Tyr Val Gly Asp Asp
545                 550                 555                 560

Val Lys Val Pro Asp Ala Gly Ala Leu Gly Val Val Ala Ile Val Glu
                    565                 570                 575

Gly Phe Thr Lys
            580

<210> SEQ ID NO 7
<211> LENGTH: 291
<212> TYPE: PRT
<213> ORGANISM: Danio rerio
<220> FEATURE:
<221> NAME/KEY: MISC_FEATURE
<222> LOCATION: (1)..(291)
<223> OTHER INFORMATION: D. rerio aquaporin 9 (Drer_T3) amino acid
      sequence

<400> SEQUENCE: 7

Met Glu Tyr Leu Glu Asn Ile Arg Asn Leu Arg Gly Arg Cys Val Leu
1               5                   10                  15

Arg Arg Asp Ile Ile Arg Glu Phe Leu Ala Glu Leu Leu Gly Thr Phe
                20                  25                  30

Val Leu Ile Leu Phe Gly Cys Gly Ser Val Ala Gln Thr Val Leu Ser
            35                  40                  45

Arg Glu Ala Lys Gly Gln Leu Leu Thr Ile His Phe Gly Phe Thr Leu
        50                  55                  60

Gly Val Met Leu Ala Val Tyr Met Ala Gly Gly Val Ser Gly Gly His
65                  70                  75                  80

Val Asn Pro Ala Val Ser Leu Ala Met Val Val Leu Arg Lys Leu Pro
                85                  90                  95

Leu Lys Lys Phe Pro Val Tyr Val Leu Ala Gln Phe Leu Gly Ala Phe
                100                 105                 110

Phe Gly Ser Cys Ala Val Tyr Cys Leu Tyr Tyr Asp Ala Phe Thr Glu
```

```
            115                 120                 125
Phe Ala Asn Gly Glu Leu Ala Val Thr Gly Pro Asn Val Thr Ala Gly
    130                 135                 140
Ile Phe Ala Ser Tyr Pro Arg Glu Gly Leu Ser Leu Leu Asn Gly Phe
145                 150                 155                 160
Ile Asp Gln Val Ile Gly Ala Gly Ala Leu Val Leu Cys Ile Leu Ala
                165                 170                 175
Val Val Asp Lys Lys Asn Ile Gly Ala Pro Lys Gly Met Glu Pro Leu
            180                 185                 190
Leu Val Gly Leu Ser Ile Leu Ala Ile Gly Val Ser Met Ala Leu Asn
        195                 200                 205
Cys Gly Tyr Pro Ile Asn Pro Ala Arg Asp Leu Gly Pro Arg Leu Phe
    210                 215                 220
Thr Ala Ile Ala Gly Trp Gly Leu Thr Val Phe Ser Ala Gly Asn Gly
225                 230                 235                 240
Trp Trp Trp Val Pro Val Val Gly Pro Met Val Gly Gly Val Val Gly
                245                 250                 255
Ala Ala Ile Tyr Phe Leu Met Ile Glu Met His His Pro Glu Asn Asp
                260                 265                 270
Lys Asn Leu Glu Asp Asp Asn Ser Leu Lys Asp Lys Tyr Glu Leu Asn
            275                 280                 285
Thr Val Asn
    290

<210> SEQ ID NO 8
<211> LENGTH: 592
<212> TYPE: PRT
<213> ORGANISM: Zygosaccharomyces rouxii
<220> FEATURE:
<221> NAME/KEY: MISC_FEATURE
<222> LOCATION: (1)..(592)
<223> OTHER INFORMATION: Z. rouxii ZYRO0E01210p (Zrou_T5) amino acid
      sequence

<400> SEQUENCE: 8

Met Gly Lys Arg Thr Gln Gly Phe Met Asp Tyr Val Phe Ser Arg Thr
1               5                   10                  15
Ser Thr Ala Gly Leu Lys Gly Ala Arg Leu Arg Tyr Thr Ala Ala Ala
            20                  25                  30
Val Ala Val Ile Gly Phe Ala Leu Phe Gly Tyr Asp Gln Gly Leu Met
        35                  40                  45
Ser Gly Leu Ile Thr Gly Asp Gln Phe Asn Lys Glu Phe Pro Pro Thr
    50                  55                  60
Lys Ser Asn Gly Asp Asn Asp Arg Tyr Ala Ser Val Ile Gln Gly Ala
65              70                  75                  80
Val Thr Ala Cys Tyr Glu Ile Gly Cys Phe Phe Gly Ser Leu Phe Val
                85                  90                  95
Leu Phe Phe Gly Asp Ala Ile Gly Arg Lys Pro Leu Ile Ile Phe Gly
                100                 105                 110
Ala Ile Ile Val Ile Gly Thr Val Ile Ser Thr Ala Pro Phe His
            115                 120                 125
His Ala Trp Gly Leu Gly Gln Phe Val Val Gly Arg Val Ile Thr Gly
            130                 135                 140
Val Gly Thr Gly Phe Asn Thr Ser Thr Ile Pro Val Trp Gln Ser Glu
145                 150                 155                 160
Met Thr Lys Pro Asn Ile Arg Gly Ala Met Ile Asn Leu Asp Gly Ser
```

```
                165                 170                 175
Val Ile Ala Phe Gly Thr Met Ile Ala Tyr Trp Leu Asp Phe Gly Phe
            180                 185                 190

Ser Phe Ile Asn Ser Ser Val Gln Trp Arg Phe Pro Val Ser Val Gln
            195                 200                 205

Ile Ile Phe Ala Leu Val Leu Leu Phe Gly Ile Val Arg Met Pro Glu
            210                 215                 220

Ser Pro Arg Trp Leu Met Ala Lys Lys Arg Pro Ala Glu Ala Arg Tyr
225                 230                 235                 240

Val Leu Ala Cys Leu Asn Asp Leu Pro Glu Asn Asp Asp Ala Ile Leu
                245                 250                 255

Ala Glu Met Thr Ser Leu His Glu Ala Val Asn Arg Ser Ser Asn Gln
            260                 265                 270

Lys Ser Gln Met Lys Ser Leu Phe Ser Met Gly Lys Gln Gln Asn Phe
            275                 280                 285

Ser Arg Ala Leu Ile Ala Ser Ser Thr Gln Phe Phe Gln Gln Phe Thr
            290                 295                 300

Gly Cys Asn Ala Ala Ile Tyr Tyr Ser Thr Val Leu Phe Gln Thr Thr
305                 310                 315                 320

Val Gln Leu Asp Arg Leu Leu Ala Met Ile Leu Gly Gly Val Phe Ala
                325                 330                 335

Thr Val Tyr Thr Leu Ser Thr Leu Pro Ser Phe Tyr Leu Val Glu Lys
                340                 345                 350

Val Gly Arg Arg Lys Met Phe Phe Gly Ala Leu Gly Gln Gly Ile
            355                 360                 365

Ser Phe Ile Ile Thr Phe Ala Cys Leu Val Asn Pro Thr Lys Gln Asn
            370                 375                 380

Ala Lys Gly Ala Ala Val Gly Leu Tyr Leu Phe Ile Ile Cys Phe Gly
385                 390                 395                 400

Leu Ala Ile Leu Glu Leu Pro Trp Ile Tyr Pro Pro Glu Ile Ala Ser
                405                 410                 415

Met Arg Val Arg Ala Ala Thr Asn Ala Met Ser Thr Cys Thr Asn Trp
                420                 425                 430

Val Thr Asn Phe Ala Val Val Met Phe Thr Pro Val Phe Ile Gln Thr
            435                 440                 445

Ser Gln Trp Gly Cys Tyr Leu Phe Phe Ala Val Met Asn Phe Ile Tyr
            450                 455                 460

Leu Pro Val Ile Phe Phe Phe Tyr Pro Glu Thr Ala Gly Arg Ser Leu
465                 470                 475                 480

Glu Glu Ile Asp Ile Ile Phe Ala Lys Ala His Val Asp Gly Thr Leu
                485                 490                 495

Pro Trp Met Val Ala His Arg Leu Pro Lys Leu Ser Met Thr Glu Val
                500                 505                 510

Glu Asp Tyr Ser Gln Ser Leu Gly Leu His Asp Asp Glu Asn Glu Lys
            515                 520                 525

Glu Glu Tyr Asp Glu Lys Glu Ala Glu Ala Asn Ala Ala Leu Phe Gln
            530                 535                 540

Val Glu Thr Ser Ser Lys Ser Pro Ser Ser Asn Arg Lys Asp Asp Asp
545                 550                 555                 560

Ala Pro Ile Glu His Asn Glu Val Gln Glu Ser Asn Asp Asn Ser Ser
                565                 570                 575

Asn Ser Ser Asn Val Glu Ala Pro Ile Pro Val His His Asn Asp Pro
            580                 585                 590
```

```
<210> SEQ ID NO 9
<211> LENGTH: 97
<212> TYPE: PRT
<213> ORGANISM: Escherichia coli
<220> FEATURE:
<221> NAME/KEY: MISC_FEATURE
<222> LOCATION: (1)..(97)
<223> OTHER INFORMATION: groES from E. coli

<400> SEQUENCE: 9

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala

<210> SEQ ID NO 10
<211> LENGTH: 548
<212> TYPE: PRT
<213> ORGANISM: Escherichia coli
<220> FEATURE:
<221> NAME/KEY: MISC_FEATURE
<222> LOCATION: (1)..(548)
<223> OTHER INFORMATION: groEL from E. coli

<400> SEQUENCE: 10

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
```

```
                180                 185                 190
Met Gln Phe Asp Arg Gly Tyr Leu Ser Pro Tyr Phe Ile Asn Lys Pro
            195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 11
<211> LENGTH: 459
<212> TYPE: PRT
<213> ORGANISM: Thiobacillus denitrificans
<220> FEATURE:
<221> NAME/KEY: MISC_FEATURE
<222> LOCATION: (1)..(459)
```

<223> OTHER INFORMATION: RubisCO cbbM gene from Thiobacillus denitrificans

<400> SEQUENCE: 11

```
Met Asp Gln Ser Ala Arg Tyr Ala Asp Leu Ser Leu Lys Glu Glu Asp
1               5                   10                  15

Leu Ile Lys Gly Gly Arg His Ile Leu Val Ala Tyr Lys Met Lys Pro
            20                  25                  30

Lys Ser Gly Tyr Gly Tyr Leu Glu Ala Ala His Phe Ala Ala Glu
        35                  40                  45

Ser Ser Thr Gly Thr Asn Val Glu Val Ser Thr Thr Asp Asp Phe Thr
50                  55                  60

Lys Gly Val Asp Ala Leu Val Tyr Tyr Ile Asp Glu Ala Ser Glu Asp
65                  70                  75                  80

Met Arg Ile Ala Tyr Pro Leu Glu Leu Phe Asp Arg Asn Val Thr Asp
                85                  90                  95

Gly Arg Phe Met Leu Val Ser Phe Leu Thr Leu Ala Ile Gly Asn Asn
            100                 105                 110

Gln Gly Met Gly Asp Ile Glu His Ala Lys Met Ile Asp Phe Tyr Val
        115                 120                 125

Pro Glu Arg Cys Ile Gln Met Phe Asp Gly Pro Ala Thr Asp Ile Ser
130                 135                 140

Asn Leu Trp Arg Ile Leu Gly Arg Pro Val Val Asn Gly Gly Tyr Ile
145                 150                 155                 160

Ala Gly Thr Ile Ile Lys Pro Lys Leu Gly Leu Arg Pro Glu Pro Phe
                165                 170                 175

Ala Lys Ala Ala Tyr Gln Phe Trp Leu Gly Gly Asp Phe Ile Lys Asn
            180                 185                 190

Asp Glu Pro Gln Gly Asn Gln Val Phe Cys Pro Leu Lys Lys Val Leu
        195                 200                 205

Pro Leu Val Tyr Asp Ala Met Lys Arg Ala Gln Asp Thr Gly Gln
210                 215                 220

Ala Lys Leu Phe Ser Met Asn Ile Thr Ala Asp Asp His Tyr Glu Met
225                 230                 235                 240

Cys Ala Arg Ala Asp Tyr Ala Leu Glu Val Phe Gly Pro Asp Ala Asp
                245                 250                 255

Lys Leu Ala Phe Leu Val Asp Gly Tyr Val Gly Gly Pro Gly Met Val
            260                 265                 270

Thr Thr Ala Arg Arg Gln Tyr Pro Gly Gln Tyr Leu His Tyr His Arg
        275                 280                 285

Ala Gly His Gly Ala Val Thr Ser Pro Ser Ala Lys Arg Gly Tyr Thr
290                 295                 300

Ala Phe Val Leu Ala Lys Met Ser Arg Leu Gln Gly Ala Ser Gly Ile
305                 310                 315                 320

His Val Gly Thr Met Gly Tyr Gly Lys Met Glu Gly Glu Gly Asp Asp
                325                 330                 335

Lys Ile Ile Ala Tyr Met Ile Glu Arg Asp Glu Cys Gln Gly Pro Val
            340                 345                 350

Tyr Phe Gln Lys Trp Tyr Gly Met Lys Pro Thr Thr Pro Ile Ile Ser
        355                 360                 365

Gly Gly Met Asn Ala Leu Arg Leu Pro Gly Phe Phe Glu Asn Leu Gly
370                 375                 380

His Gly Asn Val Ile Asn Thr Ala Gly Gly Gly Ser Tyr Gly His Ile
385                 390                 395                 400
```

```
Asp Ser Pro Ala Ala Gly Ala Ile Ser Leu Arg Gln Ser Tyr Glu Cys
                405                 410                 415

Trp Lys Gln Gly Ala Asp Pro Ile Glu Phe Ala Lys Glu His Lys Glu
            420                 425                 430

Phe Ala Arg Ala Phe Glu Ser Phe Pro Lys Asp Ala Asp Lys Leu Phe
        435                 440                 445

Pro Gly Trp Arg Glu Lys Leu Gly Val His Ser
    450                 455

<210> SEQ ID NO 12
<211> LENGTH: 352
<212> TYPE: PRT
<213> ORGANISM: Spinacia oleracea
<220> FEATURE:
<221> NAME/KEY: MISC_FEATURE
<222> LOCATION: (1)..(352)
<223> OTHER INFORMATION: PRK spinacia

<400> SEQUENCE: 12

Met Ser Gln Gln Gln Thr Ile Val Ile Gly Leu Ala Ala Asp Ser Gly
1               5                   10                  15

Cys Gly Lys Ser Thr Phe Met Arg Arg Leu Thr Ser Val Phe Gly Gly
            20                  25                  30

Ala Ala Glu Pro Pro Lys Gly Gly Asn Pro Asp Ser Asn Thr Leu Ile
        35                  40                  45

Ser Asp Thr Thr Thr Val Ile Cys Leu Asp Asp Phe His Ser Leu Asp
    50                  55                  60

Arg Asn Gly Arg Lys Val Glu Lys Val Thr Ala Leu Asp Pro Lys Ala
65                  70                  75                  80

Asn Asp Phe Asp Leu Met Tyr Glu Gln Val Lys Ala Leu Lys Glu Gly
                85                  90                  95

Lys Ala Val Asp Lys Pro Ile Tyr Asn His Val Ser Gly Leu Leu Asp
            100                 105                 110

Pro Pro Glu Leu Ile Gln Pro Pro Lys Ile Leu Val Ile Glu Gly Leu
        115                 120                 125

His Pro Met Tyr Asp Ala Arg Val Arg Glu Leu Leu Asp Phe Ser Ile
    130                 135                 140

Tyr Leu Asp Ile Ser Asn Glu Val Lys Phe Ala Trp Lys Ile Gln Arg
145                 150                 155                 160

Asp Met Lys Glu Arg Gly His Ser Leu Glu Ser Ile Lys Ala Ser Ile
                165                 170                 175

Glu Ser Arg Lys Pro Asp Phe Asp Ala Tyr Ile Asp Pro Gln Lys Gln
            180                 185                 190

His Ala Asp Val Val Ile Glu Val Leu Pro Thr Glu Leu Ile Pro Asp
    195                 200                 205

Asp Asp Glu Gly Lys Val Leu Arg Val Arg Met Ile Gln Lys Glu Gly
210                 215                 220

Val Lys Phe Phe Asn Pro Val Tyr Leu Phe Asp Glu Gly Ser Thr Ile
225                 230                 235                 240

Ser Trp Ile Pro Cys Gly Arg Lys Leu Thr Cys Ser Tyr Pro Gly Ile
                245                 250                 255

Lys Phe Ser Tyr Gly Pro Asp Thr Phe Tyr Gly Asn Glu Val Thr Val
            260                 265                 270

Val Glu Met Asp Gly Met Phe Asp Arg Leu Asp Glu Leu Ile Tyr Val
        275                 280                 285
```

Glu Ser His Leu Ser Asn Leu Ser Thr Lys Phe Tyr Gly Glu Val Thr
    290                 295                 300

Gln Gln Met Leu Lys His Gln Asn Phe Pro Gly Ser Asn Asn Gly Thr
305                 310                 315                 320

Gly Phe Phe Gln Thr Ile Ile Gly Leu Lys Ile Arg Asp Leu Phe Glu
                325                 330                 335

Gln Leu Val Ala Ser Arg Ser Thr Ala Thr Ala Ala Lys Ala
            340                 345                 350

<210> SEQ ID NO 13
<211> LENGTH: 367
<212> TYPE: PRT
<213> ORGANISM: Escherichia coli
<220> FEATURE:
<221> NAME/KEY: MISC_FEATURE
<222> LOCATION: (1)..(367)
<223> OTHER INFORMATION: E. coli glycerol dehydrogenase (Ec_gldA) amino
      acid sequence

<400> SEQUENCE: 13

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

```
Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
                355                 360                 365

<210> SEQ ID NO 14
<211> LENGTH: 584
<212> TYPE: PRT
<213> ORGANISM: Saccharomyces cerevisiae
<220> FEATURE:
<221> NAME/KEY: MISC_FEATURE
<222> LOCATION: (1)..(584)
<223> OTHER INFORMATION: S. cerevisiae dihydroxyacetone kinase (S.
      cerevisiae DAK1) amino acid sequence

<400> SEQUENCE: 14

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80

Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
    210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
            260                 265                 270
```

```
Gly Gly Val Ser Asn Phe Val Ile Ser Ser Ile Thr Ser Lys Thr Thr
            275                 280                 285

Asp Phe Leu Lys Glu Asn Tyr Asn Ile Thr Pro Val Gln Thr Ile Ala
290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
                340                 345                 350

Trp Pro Ile Ala Asp Phe Glu Lys Thr Ser Ala Pro Ser Val Asn Asp
                355                 360                 365

Asp Leu Leu His Asn Glu Val Thr Ala Lys Ala Val Gly Thr Tyr Asp
370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
                420                 425                 430

Leu Asp Lys Leu Ser Lys Asp Ser Leu Ser Gln Ala Val Ala Gln Ile
                435                 440                 445

Ser Asp Phe Ile Glu Gly Ser Met Gly Gly Thr Ser Gly Gly Leu Tyr
                450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
                500                 505                 510

Ser Thr Met Ile Asp Ala Leu Glu Pro Phe Val Lys Glu Phe Thr Ala
                515                 520                 525

Ser Lys Asp Phe Asn Lys Ala Val Lys Ala Ala Glu Glu Gly Ala Lys
                530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575

Leu Lys Gly Val Gln Ser Ala Leu
            580

<210> SEQ ID NO 15
<211> LENGTH: 12
<212> TYPE: PRT
<213> ORGANISM: Spinacia oleracea
<220> FEATURE:
<221> NAME/KEY: MISC_FEATURE
<222> LOCATION: (1)..(12)
<223> OTHER INFORMATION: PRK motif

<400> SEQUENCE: 15

Asn Asn Asn Ala Thr Thr Gly Thr Asn Asn Asn
1               5                   10

<210> SEQ ID NO 16
<211> LENGTH: 8
<212> TYPE: PRT
```

```
<213> ORGANISM: Spinacia oleracea
<220> FEATURE:
<221> NAME/KEY: MISC_FEATURE
<222> LOCATION: (1)..(8)
<223> OTHER INFORMATION: PRK motif

<400> SEQUENCE: 16

Thr Cys Gly Thr Thr Tyr Ala Gly
1               5

<210> SEQ ID NO 17
<211> LENGTH: 561
<212> TYPE: PRT
<213> ORGANISM: Punctularia strigosozonata
<220> FEATURE:
<221> NAME/KEY: MISC_FEATURE
<222> LOCATION: (1)..(561)
<223> OTHER INFORMATION: Punctularia strigosozonata glucoamylase

<400> SEQUENCE: 17
```

Ser Ser Lys Ser Val Ser Ala Tyr Ile Ser Ser Glu Ser Pro Ile Ala
1               5                   10                  15

His Ser Lys Leu Leu Asp Asn Ile Gly Pro Asp Gly Ala Lys Ala Pro
            20                  25                  30

Gly Ala Phe Pro Gly Val Val Ala Ser Pro Ser Thr Asp Asn Pro
        35                  40                  45

Asn Tyr Tyr Tyr Ser Trp Ile Arg Asp Ser Ser Leu Val Phe Lys Thr
    50                  55                  60

Leu Ile Asp Asp Tyr Val Asn Gly Lys Asn Thr Ser Lys Ser Leu Arg
65                  70                  75                  80

Ser Leu Ile Asp Asp Phe Val Thr Ala Ser Ser Val Phe Gln Gln Thr
                85                  90                  95

Pro Asn Pro Ser Gly Asn Val Ser Thr Gly Leu Gly Glu Pro Lys
            100                 105                 110

Phe Tyr Val Asn Glu Thr Ala Phe Leu Asp Ser Trp Gly Arg Pro Gln
        115                 120                 125

Arg Asp Gly Pro Ala Leu Arg Ser Thr Ala Leu Ile Thr Tyr Ala Asn
    130                 135                 140

Tyr Leu Leu Asp Asn Asp Asn Thr Thr Trp Val Lys Asp Thr Leu Trp
145                 150                 155                 160

Pro Ile Ile Glu Leu Asp Val Asn Tyr Val Ser Asp Phe Trp Asn Tyr
                165                 170                 175

Thr Thr Phe Asp Leu Trp Glu Glu Val Ala Ser Ser Phe Phe Thr
            180                 185                 190

Thr Ala Val Gln His Arg Ala Leu Arg Gln Ala Ser Lys Leu Ala Lys
        195                 200                 205

Thr Leu Asp Lys Thr Asp Asn Ile Asp Ser Trp Asn Thr Gln Ala Asp
    210                 215                 220

Asn Val Leu Cys Phe Leu Gln Ser Tyr Trp Asn Gly Ser Ala Ile Ile
225                 230                 235                 240

Ala Asn Thr Gly Gly Gly Arg Ser Gly Ile Asp Ala Asn Thr Val Leu
                245                 250                 255

Ala Ser Ile His Thr Phe Asp Ser Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Glu Ile Asn Ser Gly Ile Asp Pro Asn
    290                 295                 300

```
Ala Ala Val Ala Thr Gly Arg Tyr Pro Glu Asp Val Phe Tyr Asp Gly
305                 310                 315                 320

Asn Pro Trp Tyr Leu Ala Thr Ala Ala Ala Glu Gln Leu Tyr Asp
            325                 330                 335

Ala Leu Tyr Val Trp Asn Thr Thr Gly Ser Leu Glu Ile Thr Asp Ile
            340                 345                 350

Ser Leu Pro Phe Phe Gln Gln Phe Asp Ser Asp Val Lys Thr Gly Thr
            355                 360                 365

Tyr Ser Asp Asp Asp Thr Phe Asp Ser Leu Ile Ser Ser Ile Gln Ser
        370                 375                 380

Phe Ala Asp Gly Phe Leu Glu Ile His Ala Lys Tyr Thr Pro Asp Asp
385                 390                 395                 400

Gly Ala Leu Ser Glu Glu Phe Ser Lys Thr Asp Gly Ser Gln Thr Ser
                405                 410                 415

Ala Ala Asp Leu Thr Trp Ser Tyr Ala Ala Ala Leu Thr Ala Phe Asp
            420                 425                 430

Ala Arg Ser Arg Asp Ala Ala Val Lys Trp Gly Ala Lys Gly Leu Gln
        435                 440                 445

Val Pro Asp Gly Thr Cys Lys Thr Asn Glu Gly Gly Asp Asp Gly Leu
    450                 455                 460

Gly Val Pro Val Thr Phe Leu Val Lys Asp Ala Glu Thr Val Glu Gly
465                 470                 475                 480

Gln Ser Val Tyr Ile Thr Gly Ser Ile Ala Thr Leu Lys Ser Trp Ser
                485                 490                 495

Pro Asp Asp Ala Leu Leu Met Ser Pro Ser Asp Tyr Pro Thr Trp Thr
            500                 505                 510

Leu Thr Val Asn Leu Ser Ala Ser Glu Ser Val Gln Tyr Lys Tyr Ile
        515                 520                 525

Lys Lys Asp Thr Ala Gly Thr Val Ile Trp Glu Ser Asp Pro Asn Asn
    530                 535                 540

Ser Leu Leu Val Pro Ser Gly Gly Ser Val Thr Thr Asp Asp Thr Trp
545                 550                 555                 560

Arg

<210> SEQ ID NO 18
<211> LENGTH: 578
<212> TYPE: PRT
<213> ORGANISM: Punctularia strigosozonata
<220> FEATURE:
<221> NAME/KEY: MISC_FEATURE
<222> LOCATION: (1)..(578)
<223> OTHER INFORMATION: Punctularia strigosozonata glucoamylase with
      native signal sequence FGA09

<400> SEQUENCE: 18

Met Leu Ser Ser Leu Ile Val Ser Gly Leu Leu Ala Ser Gly Val Cys
1               5                   10                  15

Ala Ser Ser Lys Ser Val Ser Ala Tyr Ile Ser Ser Glu Ser Pro Ile
            20                  25                  30

Ala His Ser Lys Leu Leu Asp Asn Ile Gly Pro Asp Gly Ala Lys Ala
        35                  40                  45

Pro Gly Ala Phe Pro Gly Val Val Ala Ser Pro Ser Thr Asp Asn
    50                  55                  60

Pro Asn Tyr Tyr Tyr Ser Trp Ile Arg Asp Ser Ser Leu Val Phe Lys
65                  70                  75                  80
```

```
Thr Leu Ile Asp Asp Tyr Val Asn Gly Lys Asn Thr Ser Lys Ser Leu
                85                  90                  95

Arg Ser Leu Ile Asp Asp Phe Val Thr Ala Ser Ser Val Phe Gln Gln
            100                 105                 110

Thr Pro Asn Pro Ser Gly Asn Val Ser Thr Gly Gly Leu Gly Glu Pro
        115                 120                 125

Lys Phe Tyr Val Asn Glu Thr Ala Phe Leu Asp Ser Trp Gly Arg Pro
    130                 135                 140

Gln Arg Asp Gly Pro Ala Leu Arg Ser Thr Ala Leu Ile Thr Tyr Ala
145                 150                 155                 160

Asn Tyr Leu Leu Asp Asn Asp Asn Thr Thr Trp Val Lys Asp Thr Leu
                165                 170                 175

Trp Pro Ile Ile Glu Leu Asp Val Asn Tyr Val Ser Asp Phe Trp Asn
            180                 185                 190

Tyr Thr Thr Phe Asp Leu Trp Glu Glu Val Ala Ser Ser Ser Phe Phe
        195                 200                 205

Thr Thr Ala Val Gln His Arg Ala Leu Arg Gln Ala Ser Lys Leu Ala
    210                 215                 220

Lys Thr Leu Asp Lys Thr Asp Asn Ile Asp Ser Trp Asn Thr Gln Ala
225                 230                 235                 240

Asp Asn Val Leu Cys Phe Leu Gln Ser Tyr Trp Asn Gly Ser Ala Ile
                245                 250                 255

Ile Ala Asn Thr Gly Gly Gly Arg Gly Ile Asp Ala Asn Thr Val
            260                 265                 270

Leu Ala Ser Ile His Thr Phe Asp Ser Ala Gly Cys Asp Ala Thr
        275                 280                 285

Thr Phe Gln Pro Cys Ser Asp Lys Ala Leu Ser Asn Leu Lys Val Tyr
    290                 295                 300

Val Asp Ala Phe Arg Ser Ile Tyr Glu Ile Asn Ser Gly Ile Asp Pro
305                 310                 315                 320

Asn Ala Ala Val Ala Thr Gly Arg Tyr Pro Glu Asp Val Phe Tyr Asp
                325                 330                 335

Gly Asn Pro Trp Tyr Leu Ala Thr Ala Ala Val Ala Glu Gln Leu Tyr
            340                 345                 350

Asp Ala Leu Tyr Val Trp Asn Thr Thr Gly Ser Leu Glu Ile Thr Asp
        355                 360                 365

Ile Ser Leu Pro Phe Phe Gln Gln Phe Asp Ser Asp Val Lys Thr Gly
    370                 375                 380

Thr Tyr Ser Asp Asp Thr Phe Asp Ser Leu Ile Ser Ser Ile Gln
385                 390                 395                 400

Ser Phe Ala Asp Gly Phe Leu Glu Ile His Ala Lys Tyr Thr Pro Asp
                405                 410                 415

Asp Gly Ala Leu Ser Glu Glu Phe Ser Lys Thr Asp Gly Ser Gln Thr
            420                 425                 430

Ser Ala Ala Asp Leu Thr Trp Ser Tyr Ala Ala Leu Thr Ala Phe
        435                 440                 445

Asp Ala Arg Ser Arg Asp Ala Ala Val Lys Trp Gly Ala Lys Gly Leu
    450                 455                 460

Gln Val Pro Asp Gly Thr Cys Lys Thr Asn Glu Gly Gly Asp Asp Gly
465                 470                 475                 480

Leu Gly Val Pro Val Thr Phe Leu Val Lys Asp Ala Glu Thr Val Glu
                485                 490                 495

Gly Gln Ser Val Tyr Ile Thr Gly Ser Ile Ala Thr Leu Lys Ser Trp
```

```
                500             505             510
Ser Pro Asp Asp Ala Leu Leu Met Ser Pro Ser Asp Tyr Pro Thr Trp
        515                 520             525

Thr Leu Thr Val Asn Leu Ser Ala Ser Glu Ser Val Gln Tyr Lys Tyr
    530                 535             540

Ile Lys Lys Asp Thr Ala Gly Thr Val Ile Trp Glu Ser Asp Pro Asn
545                 550             555                 560

Asn Ser Leu Leu Val Pro Ser Gly Gly Ser Val Thr Thr Asp Asp Thr
                565             570             575

Trp Arg

<210> SEQ ID NO 19
<211> LENGTH: 580
<212> TYPE: PRT
<213> ORGANISM: Artificial
<220> FEATURE:
<223> OTHER INFORMATION: Punctularia strigosozonata glucoamylase with Sc
      alpha mating factor signal sequence

<400> SEQUENCE: 19

Met Arg Phe Pro Ser Ile Phe Thr Ala Val Leu Phe Ala Ala Ser Ser
1               5                   10                  15

Ala Leu Ala Ser Ser Lys Ser Val Ser Ala Tyr Ile Ser Ser Glu Ser
            20                  25                  30

Pro Ile Ala His Ser Lys Leu Leu Asp Asn Ile Gly Pro Asp Gly Ala
        35                  40                  45

Lys Ala Pro Gly Ala Phe Pro Gly Val Val Ala Ser Pro Ser Thr
50                  55                  60

Asp Asn Pro Asn Tyr Tyr Tyr Ser Trp Ile Arg Asp Ser Ser Leu Val
65                  70                  75                  80

Phe Lys Thr Leu Ile Asp Asp Tyr Val Asn Gly Lys Asn Thr Ser Lys
                85                  90                  95

Ser Leu Arg Ser Leu Ile Asp Asp Phe Val Thr Ala Ser Ser Val Phe
            100                 105                 110

Gln Gln Thr Pro Asn Pro Ser Gly Asn Val Ser Thr Gly Gly Leu Gly
        115                 120                 125

Glu Pro Lys Phe Tyr Val Asn Glu Thr Ala Phe Leu Asp Ser Trp Gly
    130                 135                 140

Arg Pro Gln Arg Asp Gly Pro Ala Leu Arg Ser Thr Ala Leu Ile Thr
145                 150                 155                 160

Tyr Ala Asn Tyr Leu Leu Asp Asn Asp Asn Thr Thr Trp Val Lys Asp
                165                 170                 175

Thr Leu Trp Pro Ile Ile Glu Leu Asp Val Asn Tyr Val Ser Asp Phe
            180                 185                 190

Trp Asn Tyr Thr Thr Phe Asp Leu Trp Glu Glu Val Ala Ser Ser Ser
        195                 200                 205

Phe Phe Thr Thr Ala Val Gln His Arg Ala Leu Arg Gln Ala Ser Lys
    210                 215                 220

Leu Ala Lys Thr Leu Asp Lys Thr Asp Asn Ile Asp Ser Trp Asn Thr
225                 230                 235                 240

Gln Ala Asp Asn Val Leu Cys Phe Leu Gln Ser Tyr Trp Asn Gly Ser
                245                 250                 255

Ala Ile Ile Ala Asn Thr Gly Gly Gly Arg Ser Gly Ile Asp Ala Asn
            260                 265                 270

Thr Val Leu Ala Ser Ile His Thr Phe Asp Ser Ser Ala Gly Cys Asp
```

```
        275                 280                 285

Ala Thr Thr Phe Gln Pro Cys Ser Asp Lys Ala Leu Ser Asn Leu Lys
    290                 295                 300

Val Tyr Val Asp Ala Phe Arg Ser Ile Tyr Glu Ile Asn Ser Gly Ile
305                 310                 315                 320

Asp Pro Asn Ala Ala Val Ala Thr Gly Arg Tyr Pro Glu Asp Val Phe
                325                 330                 335

Tyr Asp Gly Asn Pro Trp Tyr Leu Ala Thr Ala Ala Val Ala Glu Gln
            340                 345                 350

Leu Tyr Asp Ala Leu Tyr Val Trp Asn Thr Thr Gly Ser Leu Glu Ile
        355                 360                 365

Thr Asp Ile Ser Leu Pro Phe Phe Gln Gln Phe Asp Ser Asp Val Lys
    370                 375                 380

Thr Gly Thr Tyr Ser Asp Asp Asp Thr Phe Asp Ser Leu Ile Ser Ser
385                 390                 395                 400

Ile Gln Ser Phe Ala Asp Gly Phe Leu Glu Ile His Ala Lys Tyr Thr
                405                 410                 415

Pro Asp Asp Gly Ala Leu Ser Glu Glu Phe Ser Lys Thr Asp Gly Ser
            420                 425                 430

Gln Thr Ser Ala Ala Asp Leu Thr Trp Ser Tyr Ala Ala Ala Leu Thr
        435                 440                 445

Ala Phe Asp Ala Arg Ser Arg Asp Ala Ala Val Lys Trp Gly Ala Lys
    450                 455                 460

Gly Leu Gln Val Pro Asp Gly Thr Cys Lys Thr Asn Glu Gly Gly Asp
465                 470                 475                 480

Asp Gly Leu Gly Val Pro Val Thr Phe Leu Val Lys Asp Ala Glu Thr
                485                 490                 495

Val Glu Gly Gln Ser Val Tyr Ile Thr Gly Ser Ile Ala Thr Leu Lys
            500                 505                 510

Ser Trp Ser Pro Asp Asp Ala Leu Leu Met Ser Pro Ser Asp Tyr Pro
        515                 520                 525

Thr Trp Thr Leu Thr Val Asn Leu Ser Ala Ser Glu Ser Val Gln Tyr
    530                 535                 540

Lys Tyr Ile Lys Lys Asp Thr Ala Gly Thr Val Ile Trp Glu Ser Asp
545                 550                 555                 560

Pro Asn Asn Ser Leu Leu Val Pro Ser Gly Gly Ser Val Thr Thr Asp
                565                 570                 575

Asp Thr Trp Arg
            580
```

<210> SEQ ID NO 20
<211> LENGTH: 619
<212> TYPE: PRT
<213> ORGANISM: Corynascus sepedonium
<220> FEATURE:
<221> NAME/KEY: MISC_FEATURE
<222> LOCATION: (1)..(619)
<223> OTHER INFORMATION: Corynascus sepedonium glucoamylase (mature)

<400> SEQUENCE: 20

```
Arg Pro Gly Ala Ile Pro Arg Ser Gln Arg Gly Gly Ala Ile Ser Lys
1               5                   10                  15

Arg Ala Val Asp Ser Tyr Ile Glu Thr Glu Thr Pro Ile Ala Trp Glu
            20                  25                  30

Lys Leu Leu Cys Asn Ile Gly Pro Asp Gly Cys Ala Val Ser Gly Ala
        35                  40                  45
```

```
Ala Ala Gly Ala Val Ile Ala Ser Pro Ser Lys Ser Asp Pro Asp Tyr
        50                  55                  60

Trp Tyr Thr Trp Thr Arg Asp Ala Gly Leu Val Leu Thr Gly Ile Val
 65                  70                  75                  80

Asp Ser Leu Ala His Asn Tyr Ser Ala Ser Leu Gln Thr Asn Ile Gln
                     85                  90                  95

Asn Tyr Ile Ile Ala Gln Ala Lys Leu Gln Gly Val Gly Asn Pro Ser
             100                 105                 110

Gly Gly Leu Ser Asp Gly Ala Gly Leu Gly Glu Pro Lys Phe Met Val
         115                 120                 125

Asp Leu Thr Glu Phe Thr Gly Asp Trp Gly Arg Pro Gln Arg Asp Gly
     130                 135                 140

Pro Pro Leu Arg Ala Ile Ala Leu Ile Arg Tyr Ala Lys Trp Leu Val
145                 150                 155                 160

Ala Asn Gly Tyr Lys Asp Thr Ala Asn Glu Leu Val Trp Pro Val Ile
                 165                 170                 175

Gln Asn Asp Leu Ala Tyr Ala Ala Gln Tyr Trp Asn Glu Thr Gly Phe
             180                 185                 190

Asp Leu Trp Glu Glu Val Pro Gly Ser Ser Phe Phe Thr Ile Ala Ser
         195                 200                 205

Thr His Arg Ala Leu Val Glu Gly Ala Ala Leu Ala Ala Gln Leu Asp
     210                 215                 220

Thr Glu Cys Arg Ala Cys Ile Thr Val Ala Pro Gln Val Leu Cys Phe
225                 230                 235                 240

Leu Gln Thr Phe Trp Asn Pro Ser Gly Gly Tyr Val Val Ser Asn Ile
                 245                 250                 255

Asn Gly Gly Glu Gly Arg Ser Gly Lys Asp Leu Asn Ser Ile Leu Ala
             260                 265                 270

Ser Ala His Thr Phe Asp Pro Ala Ile Gly Cys Asp Ser Val Thr Phe
         275                 280                 285

Gln Pro Cys Ser Asp Lys Ala Leu Ala Asn His Lys Ala Tyr Val Asp
     290                 295                 300

Ser Phe Arg Glu Ile Tyr Gly Ile Asn Ser Gly Ile Ala Lys Gly Lys
305                 310                 315                 320

Ala Val Ala Val Gly Arg Tyr Ser Glu Asp Val Tyr Tyr Asn Gly Asn
                 325                 330                 335

Pro Trp Tyr Leu Ala Asn Phe Gly Ala Ala Glu Gln Leu Tyr Asp Ala
             340                 345                 350

Ile Tyr Val Trp Lys Glu Gln Gly Ser Ile Glu Val Thr Asp Leu Ser
         355                 360                 365

Leu Pro Phe Phe Gln Asp Leu Leu Ser Asp Ile Ser Thr Gly Thr Tyr
     370                 375                 380

Asp Ser Ser Ser Thr Tyr Gln Glu Ile Leu Asp Ala Val Ser Ala
385                 390                 395                 400

Tyr Ala Asp Gly Phe Ile Asp Val Ala Ala Gln Tyr Thr Pro Ser Asp
                 405                 410                 415

Gly Ser Leu Ala Glu Gln Phe Glu Arg Asp Ser Gly Asn Pro Ile Ser
             420                 425                 430

Ala Ala Asp Leu Thr Trp Ser Tyr Ser Ala Phe Leu Ser Ala Thr Asp
         435                 440                 445

Arg Arg Ala Gly Ile Val Pro Ala Gly Trp Ser Ala Glu Asn Gly Lys
     450                 455                 460
```

```
Thr Leu Pro Asp Ser Cys Glu Ala Ile Gln Val Ala Gly Thr Tyr Thr
465                 470                 475                 480

Gln Ala Ser Pro Thr Ala Phe Pro Pro Asn Gln Thr Pro Asn Pro Ser
            485                 490                 495

Ala Glu Thr Pro Glu Thr Pro Phe Pro Ser Ser Cys Ala Asp Ala Asn
            500                 505                 510

Glu Val Tyr Val Thr Phe Lys Gly Lys Val Thr Thr Gln Trp Gly Glu
            515                 520                 525

Ser Val Lys Val Val Gly Ser Thr Pro Glu Leu Gly Ser Trp Asp Val
            530                 535                 540

Lys Lys Ala Val Pro Leu Ser Ala Ser Ala Tyr Thr Glu Ser Asn Pro
545                 550                 555                 560

Leu Trp Lys Ile Thr Val Pro Met Lys Ala Gly Gln Ala Val Gln Tyr
                565                 570                 575

Lys Phe Ile Arg Val Asn Gly Asp Gly Lys Ala Gln Trp Glu Ser Asp
                580                 585                 590

Pro Asn Arg Thr Phe Glu Val Gly Ala Ala Gly Lys Ala Asp Gly Gly
            595                 600                 605

Cys Ser Ser Gln Thr Val Glu Gly Thr Trp Arg
    610                 615
```

```
<210> SEQ ID NO 21
<211> LENGTH: 622
<212> TYPE: PRT
<213> ORGANISM: Aspergillus niger
<220> FEATURE:
<221> NAME/KEY: MISC_FEATURE
<222> LOCATION: (1)..(622)
<223> OTHER INFORMATION: Aspergillus niger glucoamylase (mature)

<400> SEQUENCE: 21

Asn Val Ile Ser Lys Arg Ala Thr Leu Asp Ser Trp Leu Ser Asn Glu
1               5                   10                  15

Ala Thr Val Ala Arg Thr Ala Ile Leu Asn Asn Ile Gly Ala Asp Gly
                20                  25                  30

Ala Trp Val Ser Gly Ala Asp Ser Gly Ile Val Val Ala Ser Pro Ser
            35                  40                  45

Thr Asp Asn Pro Asp Tyr Phe Tyr Thr Trp Thr Arg Asp Ser Gly Leu
50                  55                  60

Val Leu Lys Thr Leu Val Asp Leu Phe Arg Asn Gly Asp Thr Ser Leu
65                  70                  75                  80

Leu Ser Thr Ile Glu Asn Tyr Ile Ser Ala Gln Ala Ile Val Gln Gly
                85                  90                  95

Ile Ser Asn Pro Ser Gly Asp Leu Ser Ser Gly Ala Gly Leu Gly Glu
            100                 105                 110

Pro Lys Phe Asn Val Asp Glu Thr Ala Tyr Thr Gly Ser Trp Gly Arg
        115                 120                 125

Pro Gln Arg Asp Gly Pro Ala Leu Arg Ala Thr Ala Met Ile Gly Phe
    130                 135                 140

Gly Gln Trp Leu Leu Asp Asn Gly Tyr Thr Ser Thr Ala Thr Asp Ile
145                 150                 155                 160

Val Trp Pro Leu Val Arg Asn Asp Leu Ser Tyr Val Ala Gln Tyr Trp
                165                 170                 175

Asn Gln Thr Gly Tyr Asp Leu Trp Glu Glu Val Asn Gly Ser Ser Phe
            180                 185                 190

Phe Thr Ile Ala Val Gln His Arg Ala Leu Val Glu Gly Ser Ala Phe
```

```
            195                 200                 205
Ala Thr Ala Val Gly Ser Ser Cys Ser Trp Cys Asp Ser Gln Ala Pro
210                 215                 220

Glu Ile Leu Cys Tyr Leu Gln Ser Phe Trp Thr Gly Ser Phe Ile Leu
225                 230                 235                 240

Ala Asn Phe Asp Ser Ser Arg Ser Gly Lys Asp Ala Asn Thr Leu Leu
                245                 250                 255

Gly Ser Ile His Thr Phe Asp Pro Glu Ala Ala Cys Asp Asp Ser Thr
            260                 265                 270

Phe Gln Pro Cys Ser Pro Arg Ala Leu Ala Asn His Lys Glu Val Val
            275                 280                 285

Asp Ser Phe Arg Ser Ile Tyr Thr Leu Asn Asp Gly Leu Ser Asp Ser
            290                 295                 300

Glu Ala Val Ala Val Gly Arg Tyr Pro Glu Asp Thr Tyr Tyr Asn Gly
305                 310                 315                 320

Asn Pro Trp Phe Leu Cys Thr Leu Ala Ala Ala Glu Gln Leu Tyr Asp
                325                 330                 335

Ala Leu Tyr Gln Trp Asp Lys Gln Gly Ser Leu Glu Val Thr Asp Val
            340                 345                 350

Ser Leu Asp Phe Phe Lys Ala Leu Tyr Ser Asp Ala Ala Thr Gly Thr
            355                 360                 365

Tyr Ser Ser Ser Ser Thr Tyr Ser Ser Ile Val Asp Ala Val Lys
370                 375                 380

Thr Phe Ala Asp Gly Phe Val Ser Ile Val Glu Thr His Ala Ala Ser
385                 390                 395                 400

Asn Gly Ser Met Ser Glu Gln Tyr Asp Lys Ser Asp Gly Glu Gln Leu
                405                 410                 415

Ser Ala Arg Asp Leu Thr Trp Ser Tyr Ala Ala Leu Leu Thr Ala Asn
            420                 425                 430

Asn Arg Arg Asn Ser Val Val Pro Ala Ser Trp Gly Glu Thr Ser Ala
            435                 440                 445

Ser Ser Val Pro Gly Thr Cys Ala Ala Thr Ser Ala Ile Gly Thr Tyr
            450                 455                 460

Ser Ser Val Thr Val Thr Ser Trp Pro Ser Ile Val Ala Thr Gly Gly
465                 470                 475                 480

Thr Thr Thr Thr Ala Thr Pro Thr Gly Ser Gly Ser Val Thr Ser Thr
                485                 490                 495

Ser Lys Thr Thr Ala Thr Ala Ser Lys Thr Ser Thr Ser Thr Ser Ser
            500                 505                 510

Thr Ser Cys Thr Thr Pro Thr Ala Val Ala Val Thr Phe Asp Leu Thr
            515                 520                 525

Ala Thr Thr Thr Tyr Gly Glu Asn Ile Tyr Leu Val Gly Ser Ile Ser
            530                 535                 540

Gln Leu Gly Asp Trp Glu Thr Ser Asp Gly Ile Ala Leu Ser Ala Asp
545                 550                 555                 560

Lys Tyr Thr Ser Ser Asp Pro Leu Trp Tyr Val Thr Val Thr Leu Pro
                565                 570                 575

Ala Gly Glu Ser Phe Glu Tyr Lys Phe Ile Arg Ile Gly Ser Asp Asp
            580                 585                 590

Ser Val Glu Trp Glu Ser Asp Pro Asn Arg Glu Tyr Thr Val Pro Gln
            595                 600                 605

Ala Cys Gly Thr Ser Thr Ala Thr Val Thr Asp Thr Trp Arg
            610                 615                 620
```

<210> SEQ ID NO 22
<211> LENGTH: 612
<212> TYPE: PRT
<213> ORGANISM: Trichoderma reesei
<220> FEATURE:
<221> NAME/KEY: MISC_FEATURE
<222> LOCATION: (1)..(612)
<223> OTHER INFORMATION: T. reesei glucoamylase (mature)

<400> SEQUENCE: 22

```
Arg Pro Gly Ser Ser Gly Leu Ser Asp Val Thr Lys Arg Ser Val Asp
1               5                   10                  15

Asp Phe Ile Ser Thr Glu Thr Pro Ile Ala Leu Asn Asn Leu Leu Cys
            20                  25                  30

Asn Val Gly Pro Asp Gly Cys Arg Ala Phe Gly Thr Ser Ala Gly Ala
        35                  40                  45

Val Ile Ala Ser Pro Ser Thr Ile Asp Pro Asp Tyr Tyr Tyr Met Trp
    50                  55                  60

Thr Arg Asp Ser Ala Leu Val Phe Lys Asn Leu Ile Asp Arg Phe Thr
65                  70                  75                  80

Glu Thr Tyr Asp Ala Gly Leu Gln Arg Arg Ile Glu Gln Tyr Ile Thr
                85                  90                  95

Ala Gln Val Thr Leu Gln Gly Leu Ser Asn Pro Ser Gly Ser Leu Ala
            100                 105                 110

Asp Gly Ser Gly Leu Gly Glu Pro Lys Phe Glu Leu Thr Leu Lys Pro
        115                 120                 125

Phe Thr Gly Asn Trp Gly Arg Pro Gln Arg Asp Gly Pro Ala Leu Arg
    130                 135                 140

Ala Ile Ala Leu Ile Gly Tyr Ser Lys Trp Leu Ile Asn Asn Asn Tyr
145                 150                 155                 160

Gln Ser Thr Val Ser Asn Val Ile Trp Pro Ile Val Arg Asn Asp Leu
                165                 170                 175

Asn Tyr Val Ala Gln Tyr Trp Asn Gln Thr Gly Phe Asp Leu Trp Glu
            180                 185                 190

Glu Val Asn Gly Ser Ser Phe Phe Thr Val Ala Asn Gln His Arg Ala
        195                 200                 205

Leu Val Glu Gly Ala Thr Leu Ala Ala Thr Leu Gly Gln Ser Gly Ser
    210                 215                 220

Ala Tyr Ser Ser Val Ala Pro Gln Val Leu Cys Phe Leu Gln Arg Phe
225                 230                 235                 240

Trp Val Ser Ser Gly Gly Tyr Val Asp Ser Asn Ile Asn Thr Asn Glu
                245                 250                 255

Gly Arg Thr Gly Lys Asp Val Asn Ser Val Leu Thr Ser Ile His Thr
            260                 265                 270

Phe Asp Pro Asn Leu Gly Cys Asp Ala Gly Thr Phe Gln Pro Cys Ser
        275                 280                 285

Asp Lys Ala Leu Ser Asn Leu Lys Val Val Asp Ser Phe Arg Ser
    290                 295                 300

Ile Tyr Gly Val Asn Lys Gly Ile Pro Ala Gly Ala Ala Val Ala Ile
305                 310                 315                 320

Gly Arg Tyr Ala Glu Asp Val Tyr Tyr Asn Gly Asn Pro Trp Tyr Leu
                325                 330                 335

Ala Thr Phe Ala Ala Ala Glu Gln Leu Tyr Asp Ala Ile Tyr Val Trp
            340                 345                 350
```

```
Lys Lys Thr Gly Ser Ile Thr Val Thr Ala Thr Ser Leu Ala Phe Phe
            355                 360                 365

Gln Glu Leu Val Pro Gly Val Thr Ala Gly Thr Tyr Ser Ser Ser Ser
    370                 375                 380

Ser Thr Phe Thr Asn Ile Ile Asn Ala Val Ser Thr Tyr Ala Asp Gly
385                 390                 395                 400

Phe Leu Ser Glu Ala Ala Lys Tyr Val Pro Ala Asp Gly Ser Leu Ala
                405                 410                 415

Glu Gln Phe Asp Arg Asn Ser Gly Thr Pro Leu Ser Ala Leu His Leu
            420                 425                 430

Thr Trp Ser Tyr Ala Ser Phe Leu Thr Ala Thr Ala Arg Arg Ala Gly
        435                 440                 445

Ile Val Pro Pro Ser Trp Ala Asn Ser Ser Ala Ser Thr Ile Pro Ser
    450                 455                 460

Thr Cys Ser Gly Ala Ser Val Val Gly Ser Tyr Ser Arg Pro Thr Ala
465                 470                 475                 480

Thr Ser Phe Pro Pro Ser Gln Thr Pro Lys Pro Gly Val Pro Ser Gly
                485                 490                 495

Thr Pro Tyr Thr Pro Leu Pro Cys Ala Thr Pro Thr Ser Val Ala Val
            500                 505                 510

Thr Phe His Glu Leu Val Ser Thr Gln Phe Gly Gln Thr Val Lys Val
        515                 520                 525

Ala Gly Asn Ala Ala Ala Leu Gly Asn Trp Ser Thr Ser Ala Ala Val
    530                 535                 540

Ala Leu Asp Ala Val Asn Tyr Ala Asp Asn His Pro Leu Trp Ile Gly
545                 550                 555                 560

Thr Val Asn Leu Glu Ala Gly Asp Val Val Glu Tyr Lys Tyr Ile Asn
                565                 570                 575

Val Gly Gln Asp Gly Ser Val Thr Trp Glu Ser Asp Pro Asn His Thr
            580                 585                 590

Tyr Thr Val Pro Ala Val Ala Cys Val Thr Gln Val Val Lys Glu Asp
        595                 600                 605

Thr Trp Gln Ser
    610

<210> SEQ ID NO 23
<211> LENGTH: 535
<212> TYPE: PRT
<213> ORGANISM: Botryotinia fuckeliana
<220> FEATURE:
<221> NAME/KEY: MISC_FEATURE
<222> LOCATION: (1)..(535)
<223> OTHER INFORMATION: Botryotinia fuckeliana glucoamylase (mature)

<400> SEQUENCE: 23

Lys Asn Leu Glu His Pro Lys Leu Ser Thr Arg Thr Gly Thr Ile
1               5                   10                  15

Asp Asp Tyr Leu Thr Ala Gln Ser Pro Ile Ser Leu Gln Gly Ile Leu
            20                  25                  30

Asn Asn Ile Gly Pro Asp Gly Ser Lys Ala Gln Gly Ala Ser Ala Gly
        35                  40                  45

Ile Val Val Ala Ser Pro Ser Thr Val Asp Pro Asn Tyr Phe Tyr Thr
    50                  55                  60

Trp Thr Arg Asp Ser Ala Leu Thr Phe Lys Tyr Leu Ile Asp Thr Gly
65                  70                  75                  80

Asn Ser Ser Leu Gln Ser Leu Ile Glu Asp Tyr Val Thr Ala Gln Ala
```

```
                        85                  90                  95
Lys Leu Gln Thr Val Glu Asn Pro Ser Gly Asp Leu Ala Thr Gly Ala
                100                 105                 110

Gly Leu Ala Glu Pro Lys Tyr Tyr Thr Asn Glu Thr Ala Phe Leu Gly
                115                 120                 125

Glu Trp Gly Arg Pro Gln Arg Asp Gly Pro Ala Leu Arg Ala Ile Ala
            130                 135                 140

Leu Ile Ser Phe Gly Asn Asp Arg Leu Thr Leu Gly Gln Asn Asp Thr
145                 150                 155                 160

Val Lys Glu Ile Ile Trp Pro Ile Val Arg Asn Asp Leu Ala Tyr Val
                165                 170                 175

Ser Gln Tyr Trp Asn Phe Ser Gly Phe Asp Leu Trp Glu Glu Ile Asn
                180                 185                 190

Gly Ser Ser Phe Phe Thr Thr Ala Val Gln His Arg Ala Leu Val Glu
                195                 200                 205

Gly Ala Lys Phe Ala Thr Ala Leu Gly Glu Ser Cys Asn Asp Cys Glu
            210                 215                 220

Glu Gln Ala Pro Glu Val Leu Cys Met Leu Gln Asp Tyr Trp Asn Gly
225                 230                 235                 240

Ala Ser Ile Asn Ser Asn Ile Gln Val Gln Ser Ser Thr Tyr Asp Arg
                245                 250                 255

Ser Gly Leu Asp Cys Asn Ser Ile Leu Thr Ser Ile His Thr Phe Asp
                260                 265                 270

Pro Asp Gln Ala Val Gly Cys Asp Ser Thr Thr Phe Gln Pro Cys Ser
            275                 280                 285

Asp Arg Ala Leu Ala Asn His Lys Val Leu Val Asp Ser Phe Arg Ser
            290                 295                 300

Ile Tyr Thr Ile Asn Ser Asn Ala Ser Thr Gly Gln Ala Ala Ala Ile
305                 310                 315                 320

Gly Arg Tyr Ala Glu Asp Val Tyr Gln Gly Gly Asn Pro Trp Tyr Ile
                325                 330                 335

Cys Thr Tyr Ala Ala Ala Glu Gln Leu Tyr Asp Ala Leu Trp Thr Tyr
                340                 345                 350

Asn Thr Thr Glu Ser Ile Thr Ile Thr Asp Ile Ser Gln Asp Phe Phe
            355                 360                 365

Thr Asp Leu Val Pro Gly Ile Glu Thr Gly Thr Phe Ala Ser Asp Ser
            370                 375                 380

Ser Gln Phe Lys Asp Ile Val Lys Ala Met Gln Asp Tyr Ala Asp Gly
385                 390                 395                 400

Phe Val Ser Ile Ala Glu Thr Tyr Thr Pro Glu Asp Gly Ala Leu Ala
                405                 410                 415

Glu Gln Phe Ser Arg Glu Asn Gly Thr Ala Leu Ser Ala Val Asp Leu
                420                 425                 430

Thr Trp Ser Tyr Ala Ser Phe Leu Thr Met Gln Arg Ala Arg Glu Gly
            435                 440                 445

Lys Ser Gly Pro Ser Trp Gly Ala Ala Ser Ala Ile Ala Lys Gly Val
            450                 455                 460

Pro Asp Lys Cys Ser Gly Gly Val Lys Gly Ala Tyr Ser Thr Pro Pro
465                 470                 475                 480

Ser Ala Thr Ala Phe Pro Gln Ser Glu Glu Gly Thr Phe Gly Thr Lys
                485                 490                 495

Thr Ser Ser Thr Ser Asp Thr Gly Thr Gly Thr Gly Thr Val Ser Gly
            500                 505                 510
```

```
Thr Ala Val Ser Ala Thr Thr Ser Lys Ser Ala Gly Asn Arg Val Met
            515                 520                 525

Pro Ile Gly Phe Phe Leu His
    530                 535

<210> SEQ ID NO 24
<211> LENGTH: 575
<212> TYPE: PRT
<213> ORGANISM: Auricularia delicata
<220> FEATURE:
<221> NAME/KEY: MISC_FEATURE
<222> LOCATION: (1)..(575)
<223> OTHER INFORMATION: Auricularia delicata Glucoamylase (mature)

<400> SEQUENCE: 24

Phe Val Ala Gln Asp Ala Arg Phe Ser Ser Gly Phe Gly Leu Thr Leu
1               5                   10                  15

Gly Lys Arg Ala Ala Val Asp Asp Tyr Val Ala Ser Glu Gly Pro Ile
            20                  25                  30

Ala Leu Lys Gly Val Leu Asp Asn Ile Gly Pro Asp Gly Pro Lys Ser
        35                  40                  45

His Gly Ala Lys Pro Gly Ile Val Val Ala Ser Pro Ser Lys Val Asp
    50                  55                  60

Pro Asp Tyr Val Phe Ala Trp Ile Arg Asp Ser Ala Leu Val Phe Lys
65                  70                  75                  80

Ala Leu Ile Asp Arg Phe Val Asp Gly Arg Asp Ala Ser Arg Leu Pro
                85                  90                  95

Leu Leu Leu Gln Phe Val Ser Ser Gln Ser Ala Ile Gln Asn Leu Asp
            100                 105                 110

Asn Arg Ser Gly Ala Ala Arg Gly Ala Gly Leu Gly Glu Pro Lys Phe
        115                 120                 125

Glu Ile Asn Gln Thr Ala Phe Asn Gly Asp Trp Gly Arg Pro Gln Arg
    130                 135                 140

Asp Gly Pro Ala Leu Arg Ala Thr Ala Leu Ile Thr Leu Ser Asn Tyr
145                 150                 155                 160

Phe Leu Ser Lys Asn Asn Ala Ser Phe Val Thr Ser Thr Leu Trp Pro
                165                 170                 175

Met Ile Gln Leu Asp Leu Asn Tyr Val Ala Thr Tyr Trp Asn Gln Pro
            180                 185                 190

Thr Phe Asp Leu Trp Glu Glu Val Asn Gly Gln Ser Phe Phe Thr Thr
        195                 200                 205

Ala Val Gln His Arg Ala Leu Arg Glu Gly Ile Ala Leu Ala Gln Thr
    210                 215                 220

Leu Gly Thr Thr Gly Ser Val Ala Thr Trp Ser Thr Gln Ala Ser Asn
225                 230                 235                 240

Val Leu Cys Tyr Leu Gln Ser Tyr Trp Thr Pro Ser Gly Ala Phe Ile
                245                 250                 255

Asn Ser Asn Thr Asn Ser Gly Arg Ser Gly Ile Asp Val Asn Ser Ile
            260                 265                 270

Leu Thr Ser Ile His Thr Phe Ser Pro Asn Thr Gly Cys Asp Ala Val
        275                 280                 285

Thr Phe Gln Pro Cys Ser Asp Lys Ala Leu Ala Gly His Leu Ala Val
    290                 295                 300

Val Asn Ser Phe Arg Gly Ser Leu Tyr Pro Ile Asn Ser Gly Ile Pro
305                 310                 315                 320
```

Ala Gly Gln Ala Val Ala Ile Gly Arg Tyr Lys Glu Asp Val Tyr Tyr
            325                 330                 335

Asn Gly Asn Pro Trp Tyr Leu Ala Thr Phe Ala Ala Glu Gln Leu
        340                 345                 350

Tyr Leu Ala Leu Phe Thr Trp Asp Gln Gln Lys Ser Ile Ala Val Thr
            355                 360                 365

Ala Ile Ser Gln Pro Phe Phe Ala Gln Phe Ile Pro Asn Ile Ala Thr
370                 375                 380

Gly Thr Tyr Ala Ser Ser Ser Gln Tyr Ala Thr Leu Thr Ser Lys
385                 390                 395                 400

Ile Arg Glu Phe Ala Asp Gly Phe Ile Ala Val Asn Gln Lys Tyr Thr
                405                 410                 415

Pro Ala Asn Gly Ala Leu Ala Glu Gln Phe Thr Arg Ala Asn Gly Thr
                420                 425                 430

Pro Ile Ser Ala Ser Asp Leu Thr Trp Ser Tyr Ala Ser Ala Leu Thr
            435                 440                 445

Ala Phe Asp Arg Arg Ala Gly Ile Val Pro Gly Ala Trp Pro Ala Thr
        450                 455                 460

Gly Leu Thr Val Ala Pro Ser Cys Ser Thr Ala Gly Gly Asn Ser
465                 470                 475                 480

Thr Ile Thr Phe Lys Val Thr Ala Gln Thr Val Phe Gly Glu Asn Ile
                485                 490                 495

Tyr Leu Thr Gly Ser Val Ala Ala Leu Lys Asn Trp Ser Pro Glu Asn
            500                 505                 510

Ala Leu Gly Pro Leu Ala Asn Pro Asn Tyr Pro Gln Trp Gln Ile Thr
        515                 520                 525

Val Thr Val Pro Ala Ser Thr Ala Ile Glu Tyr Lys Tyr Ile Arg Lys
530                 535                 540

Asn Gly Gly Ser Val Val Trp Glu Ser Asp Pro Asn Arg Ser Ile Val
545                 550                 555                 560

Ser Pro Ala Ala Gly Glu Ser Ala Thr Val Thr Asp Thr Trp Arg
            565                 570                 575

<210> SEQ ID NO 25
<211> LENGTH: 617
<212> TYPE: PRT
<213> ORGANISM: Talaromyces stipitatus
<220> FEATURE:
<221> NAME/KEY: MISC_FEATURE
<222> LOCATION: (1)..(617)
<223> OTHER INFORMATION: Taloromyces stipitatus glucoamylase (mature)

<400> SEQUENCE: 25

Ala Pro Gly Leu Ser Pro Arg Ala Ser Thr Ser Leu Asp Ala Trp Leu
1               5                   10                  15

Ala Thr Glu Thr Thr Val Ser Leu Ser Gly Ile Leu Ala Asn Ile Gly
            20                  25                  30

Ala Asp Gly Ala Tyr Ser Lys Ser Ala Lys Pro Gly Val Val Ile Ala
        35                  40                  45

Ser Pro Ser Thr Asp Asn Pro Asn Tyr Tyr Thr Trp Thr Arg Asp
    50                  55                  60

Ser Ala Leu Thr Leu Lys Val Leu Ile Asp Leu Phe Arg Asn Gly Asn
65                  70                  75                  80

Leu Gly Leu Gln Thr Val Ile Glu Glu Tyr Val Asn Ala Gln Ala Tyr
                85                  90                  95

Leu Gln Thr Val Ser Asn Pro Ser Gly Asp Leu Ser Ser Gly Ala Gly

-continued

```
                100                 105                 110
Leu Ala Glu Pro Lys Phe Asn Val Asp Met Ser Ala Phe Thr Gly Ser
            115                 120                 125

Trp Gly Arg Pro Gln Arg Asp Gly Pro Ala Leu Arg Ala Ile Ala Leu
        130                 135                 140

Ile Asp Phe Gly Asn Trp Leu Ile Glu Asn Gly Tyr Thr Ser Leu Ala
145                 150                 155                 160

Ala Asn Asn Ile Trp Pro Ile Val Arg Asn Asp Leu Ser Tyr Val Ala
                165                 170                 175

Gln Tyr Trp Ser Gln Ser Gly Phe Asp Leu Trp Glu Glu Val Asn Ser
            180                 185                 190

Met Ser Phe Phe Thr Val Ala Asn Gln His Arg Ser Leu Val Glu Gly
        195                 200                 205

Ser Thr Phe Ala Ala Lys Val Gly Ala Ser Cys Ser Trp Cys Asp Ser
    210                 215                 220

Gln Ala Pro Gln Ile Leu Cys Tyr Met Gln Thr Phe Trp Thr Gly Ser
225                 230                 235                 240

Tyr Met Asn Ala Asn Thr Gly Gly Arg Ser Gly Lys Asp Ala Asn
                245                 250                 255

Thr Val Leu Thr Ser Ile Ala Thr Phe Asp Pro Glu Ala Thr Cys Asp
            260                 265                 270

Asp Val Thr Phe Gln Pro Cys Ser Pro Arg Ala Leu Ala Asn His Lys
        275                 280                 285

Val Tyr Thr Asp Ser Phe Arg Ser Val Tyr Gly Leu Asn Ser Gly Ile
290                 295                 300

Ala Glu Gly Val Ala Val Ala Val Gly Arg Tyr Pro Glu Asp Ser Tyr
305                 310                 315                 320

Tyr Asn Gly Asn Pro Trp Phe Leu Ser Asn Leu Ala Ala Ala Glu Gln
                325                 330                 335

Leu Tyr Asp Ala Ile Tyr Gln Trp Asn Lys Ile Gly Ser Ile Thr Ile
            340                 345                 350

Thr Ser Thr Ser Leu Ala Phe Phe Lys Asp Val Tyr Ser Ser Ala Ala
        355                 360                 365

Val Gly Thr Tyr Ala Ser Gly Ser Ser Ala Phe Thr Ser Ile Ile Asn
    370                 375                 380

Ala Val Lys Thr Tyr Ala Asp Gly Tyr Ile Ser Val Val Gln Ser His
385                 390                 395                 400

Ala Met Asn Asn Gly Ser Leu Ser Glu Gln Phe Asp Lys Asn Thr Gly
                405                 410                 415

Ala Glu Leu Ser Ala Arg Asp Leu Thr Trp Ser Tyr Ala Ala Leu Leu
            420                 425                 430

Thr Ala Asn Met Arg Arg Asn Gly Val Val Pro Pro Ser Trp Gly Ala
        435                 440                 445

Ala Ser Ala Thr Ser Ile Pro Ser Ser Cys Thr Thr Gly Ser Ala Ile
    450                 455                 460

Gly Thr Tyr Ser Thr Pro Thr Ala Thr Ser Trp Pro Ser Thr Leu Thr
465                 470                 475                 480

Ser Gly Thr Gly Ser Pro Gly Ser Thr Thr Ser Ala Thr Gly Ser Val
                485                 490                 495

Ser Thr Ser Val Ser Ala Thr Thr Ser Ala Gly Ser Cys Thr Thr
            500                 505                 510

Pro Thr Ser Val Ala Val Thr Phe Asp Glu Ile Ala Thr Thr Ser Tyr
        515                 520                 525
```

Gly Glu Asn Val Tyr Ile Val Gly Ser Ile Ser Gln Leu Gly Ser Trp
            530                 535                 540

Asn Thr Ala Asn Ala Ile Ala Leu Ser Ala Ser Lys Tyr Thr Thr Ser
545                 550                 555                 560

Asn Asn Leu Trp Tyr Val Thr Ile Asn Leu Pro Ala Gly Thr Thr Phe
                565                 570                 575

Gln Tyr Lys Tyr Ile Arg Lys Glu Ser Asp Gly Thr Val Lys Trp Glu
            580                 585                 590

Ser Asp Pro Asn Arg Ser Tyr Thr Val Pro Ser Ala Cys Gly Val Ser
            595                 600                 605

Thr Ala Thr Glu Asn Asp Thr Trp Arg
            610                 615

<210> SEQ ID NO 26
<211> LENGTH: 576
<212> TYPE: PRT
<213> ORGANISM: Piriformospora indica
<220> FEATURE:
<221> NAME/KEY: MISC_FEATURE
<222> LOCATION: (1)..(576)
<223> OTHER INFORMATION: Piriformospora indica glucoamylase (mature)

<400> SEQUENCE: 26

Arg Ala Ser Pro Arg Glu Asn Pro Phe Asn Lys Arg Val Ser Tyr Thr
1               5                   10                  15

Asn Val Ala Asp Phe Asp Thr Phe Glu Thr Pro Ile Ala Leu Ala Gly
            20                  25                  30

Leu Tyr Ala Asn Ile Gly Pro Asp Gly Ala Lys Ser Gln Gly Ala Lys
        35                  40                  45

Ala Gly Val Val Ile Ala Ser Pro Ser Thr Ser Asp Pro Asp Tyr Leu
    50                  55                  60

Tyr Thr Trp Thr Arg Asp Ala Ser Leu Val Phe Lys Tyr Ile Val Asp
65                  70                  75                  80

Arg Phe Thr Ser Gly Arg Asp Ser Ser Leu Arg Thr Lys Ile Asp Asn
                85                  90                  95

Phe Val Gly His Val Gly Arg Ile Gln Gln Val Thr Asn Pro Ser Gly
            100                 105                 110

Thr Val Ser Thr Gly Gly Leu Gly Glu Pro Lys Phe Met Ile Ser Glu
        115                 120                 125

Ala Ala Phe Thr Gly Glu Trp Gly Arg Pro Gln Arg Asp Gly Pro Ala
    130                 135                 140

Leu Arg Ala Thr Thr Leu Ile Ala Tyr Ala Asn Trp Leu Arg Ala Asn
145                 150                 155                 160

Ser Asn Thr Thr His Val Gln Asn Val Leu Trp Pro Ile Ile Ser Leu
                165                 170                 175

Asp Leu Asn Tyr Val Ser Asn Asn Trp Asn Ser Thr Thr Phe Asp Leu
            180                 185                 190

Trp Glu Glu Val Ser Gly Ala Ser Phe Phe Thr Thr Ala Ala Gln His
        195                 200                 205

Arg Ala Leu Arg Glu Gly Ile Ala Leu Ala Thr Ala Leu Gly Ala Pro
    210                 215                 220

Ser Ser Thr Ile Thr Ala Trp Thr Thr Gln Ala Gln Asn Leu Leu Cys
225                 230                 235                 240

Phe Leu Gln Thr Tyr Trp Ser Pro Glu Ser Gly Phe Ile Val Ala Asn
                245                 250                 255

Val Asp Pro Ile Asn Gly Ala Ile Arg Ser Gly Lys Asp Ala Asn Thr
            260                 265                 270

Val Leu Thr Thr Ile His Thr Phe Asp Pro Ala Gly Cys Asp Ser
        275                 280                 285

Ser Thr Phe Gln Pro Cys Ser Asp Lys Ala Leu Ala Asn Leu Lys Val
    290                 295                 300

Tyr Val Asp Ser Phe Arg Ser Ile Tyr Pro Ile Asn Tyr Gly Ile Ala
305                 310                 315                 320

Ser Asn Ala Ala Val Ala Thr Gly Arg Tyr Pro Glu Asp Val Tyr Tyr
                325                 330                 335

Gly Gly Asn Pro Trp Tyr Leu Thr Thr Phe Ala Val Ala Glu Gln Leu
            340                 345                 350

Tyr Arg Ala Leu Gln Val Trp Asp Ala Glu Gly Lys Gly Ile Glu Val
        355                 360                 365

Thr Ser Ile Ser Leu Pro Phe Phe Gln Gln Phe Asn Ser Ser Ala Thr
370                 375                 380

Val Thr Thr Ile Pro Ala Gly Ser Ala Ser Tyr Thr Thr Leu Thr Asn
385                 390                 395                 400

Ala Ile Lys Thr Phe Ala Asp Gly Phe Ala Leu Lys Gly Ala Gln Phe
                405                 410                 415

Val Pro Ser Ser Gly Ala Leu Ala Glu Gln Tyr Ala Arg Asn Asp Gly
            420                 425                 430

Thr Pro Val Ser Ala Val Asp Leu Thr Trp Ser Tyr Ala Ser Val Leu
        435                 440                 445

Thr Met Phe Asp Ala His Asp Arg Leu Ala Val Asp Ser Trp Gly Ala
450                 455                 460

Ala Gly Leu Thr Val Pro Thr Thr Cys Ser Ser Gly Asp Gly Lys Ser
465                 470                 475                 480

Ala Thr Val Ile Phe Lys Glu Thr Ala Thr Ile Trp Gly Glu Asn
                485                 490                 495

Ile Tyr Leu Val Gly Asn Ile Glu Ala Leu Lys Asn Trp Asn Thr Asn
            500                 505                 510

Asn Pro Ile Gly Pro Leu Ser Thr Thr Thr Tyr Pro Val Trp Thr Thr
        515                 520                 525

Leu Val Ser Ile Pro Ala Asn Thr His Phe Glu Tyr Lys Phe Ile Arg
530                 535                 540

Lys Phe Asn Gly Thr Val Thr Trp Glu Ser Gly Ala Asn Arg Trp Asn
545                 550                 555                 560

Ala Thr Gly Ala Ala Gly Thr Arg Leu Thr Leu Asn Asn Val Trp Lys
                565                 570                 575

<210> SEQ ID NO 27
<211> LENGTH: 497
<212> TYPE: PRT
<213> ORGANISM: Saccharomycopsis fibuligera
<220> FEATURE:
<221> NAME/KEY: MISC_FEATURE
<222> LOCATION: (1)..(497)
<223> OTHER INFORMATION: Saccharomycopsis fibuligera glucoamylase
      (mature)

<400> SEQUENCE: 27

Val Pro Val Glu Leu Asp Lys Arg Asn Thr Gly His Phe Gln Ala Tyr
1               5                   10                  15

Ser Gly Tyr Thr Val Ala Arg Ser Asn Phe Thr Gln Trp Ile His Glu
            20                  25                  30

```
Gln Pro Ala Val Ser Trp Tyr Tyr Leu Gln Asn Ile Asp Tyr Pro
             35                  40                  45

Glu Gly Gln Phe Lys Ser Ala Lys Pro Gly Val Val Ala Ser Pro
 50                  55                  60

Ser Thr Ser Glu Pro Asp Tyr Phe Tyr Gln Trp Thr Arg Asp Thr Ala
 65                  70                  75                  80

Ile Thr Phe Leu Ser Leu Ile Ala Glu Val Glu Asp His Ser Phe Ser
                 85                  90                  95

Asn Thr Thr Leu Ala Lys Val Val Glu Tyr Tyr Ile Ser Asn Thr Tyr
                100                 105                 110

Thr Leu Gln Arg Val Ser Asn Pro Ser Gly Asn Phe Asp Ser Pro Asn
            115                 120                 125

His Asp Gly Leu Gly Glu Pro Lys Phe Asn Val Asp Asp Thr Ala Tyr
130                 135                 140

Thr Ala Ser Trp Gly Arg Pro Gln Asn Asp Gly Pro Ala Leu Arg Ala
145                 150                 155                 160

Tyr Ala Ile Ser Arg Tyr Leu Asn Ala Val Ala Lys His Asn Asn Gly
                165                 170                 175

Lys Leu Leu Leu Ala Gly Gln Asn Gly Ile Pro Tyr Ser Ser Ala Ser
            180                 185                 190

Asp Ile Tyr Trp Lys Ile Ile Lys Pro Asp Leu Gln His Val Ser Thr
            195                 200                 205

His Trp Ser Thr Ser Gly Phe Asp Leu Trp Glu Glu Asn Gln Gly Thr
            210                 215                 220

His Phe Phe Thr Ala Leu Val Gln Leu Lys Ala Leu Ser Tyr Gly Ile
225                 230                 235                 240

Pro Leu Ser Lys Thr Tyr Asn Asp Pro Gly Phe Thr Ser Trp Leu Glu
                245                 250                 255

Lys Gln Lys Asp Ala Leu Asn Ser Tyr Ile Asn Ser Ser Gly Phe Val
            260                 265                 270

Asn Ser Gly Lys Lys His Ile Val Glu Ser Pro Gln Leu Ser Ser Arg
            275                 280                 285

Gly Gly Leu Asp Ser Ala Thr Tyr Ile Ala Ala Leu Ile Thr His Asp
290                 295                 300

Ile Gly Asp Asp Asp Thr Tyr Thr Pro Phe Asn Val Asp Asn Ser Tyr
305                 310                 315                 320

Val Leu Asn Ser Leu Tyr Tyr Leu Leu Val Asp Asn Lys Asn Arg Tyr
                325                 330                 335

Lys Ile Asn Gly Asn Tyr Lys Ala Gly Ala Ala Val Gly Arg Tyr Pro
            340                 345                 350

Glu Asp Val Tyr Asn Gly Val Gly Thr Ser Glu Gly Asn Pro Trp Gln
            355                 360                 365

Leu Ala Thr Ala Tyr Ala Gly Gln Thr Phe Tyr Thr Leu Ala Tyr Asn
            370                 375                 380

Ser Leu Lys Asn Lys Lys Asn Leu Val Ile Glu Lys Leu Asn Tyr Asp
385                 390                 395                 400

Leu Tyr Asn Ser Phe Ile Ala Asp Leu Ser Lys Ile Asp Ser Ser Tyr
                405                 410                 415

Ala Ser Lys Asp Ser Leu Thr Leu Thr Tyr Gly Ser Asp Asn Tyr Lys
            420                 425                 430

Asn Val Ile Lys Ser Leu Leu Gln Phe Gly Asp Ser Phe Leu Lys Val
            435                 440                 445

Leu Leu Asp His Ile Asp Asp Asn Gly Gln Leu Thr Glu Glu Ile Asn
```

```
                 450               455               460
Arg Tyr Thr Gly Phe Gln Ala Gly Ala Val Ser Leu Thr Trp Ser Ser
465                 470                 475                 480

Gly Ser Leu Leu Ser Ala Asn Arg Ala Arg Asn Lys Leu Ile Glu Leu
                485                 490                 495

Leu

<210> SEQ ID NO 28
<211> LENGTH: 785
<212> TYPE: PRT
<213> ORGANISM: Saccharomyces cerevisiae
<220> FEATURE:
<221> NAME/KEY: MISC_FEATURE
<222> LOCATION: (1)..(785)
<223> OTHER INFORMATION: S. cerevisiae diastaticus glucoamylase (mature)

<400> SEQUENCE: 28

Phe Pro Thr Ala Leu Val Pro Arg Gly Ser Ser Ser Asn Ile Thr
1               5                   10                  15

Ser Ser Gly Pro Ser Ser Thr Pro Phe Ser Ser Ala Thr Glu Ser Phe
                20                  25                  30

Ser Thr Gly Thr Thr Val Thr Pro Ser Ser Ser Lys Tyr Pro Gly Ser
            35                  40                  45

Lys Thr Glu Thr Ser Val Ser Ser Thr Glu Thr Thr Ile Val Pro
50                  55                  60

Thr Thr Thr Thr Thr Ser Val Ile Thr Pro Ser Thr Thr Ile Thr
65                  70                  75                  80

Thr Thr Val Cys Ser Thr Gly Thr Asn Ser Ala Gly Glu Thr Thr Ser
                85                  90                  95

Gly Cys Ser Pro Lys Thr Ile Thr Thr Thr Val Pro Cys Ser Thr Ser
            100                 105                 110

Pro Ser Glu Thr Ala Ser Glu Ser Thr Thr Thr Ser Pro Thr Thr Pro
        115                 120                 125

Val Thr Thr Val Val Ser Thr Thr Val Val Thr Thr Glu Tyr Ser Thr
130                 135                 140

Ser Thr Lys Gln Gly Gly Glu Ile Thr Thr Thr Phe Val Thr Lys Asn
145                 150                 155                 160

Ile Pro Thr Thr Tyr Leu Thr Thr Ile Ala Pro Thr Ser Ser Val Thr
                165                 170                 175

Thr Val Thr Asn Phe Thr Pro Thr Thr Ile Thr Thr Val Cys Ser
            180                 185                 190

Thr Gly Thr Asn Ser Ala Gly Glu Thr Thr Ser Gly Cys Ser Pro Lys
        195                 200                 205

Thr Val Thr Thr Val Pro Cys Ser Thr Gly Thr Gly Glu Tyr Thr
210                 215                 220

Thr Glu Ala Thr Ala Pro Val Thr Thr Ala Val Thr Thr Val Val
225                 230                 235                 240

Thr Thr Glu Ser Ser Thr Gly Thr Asn Ser Ala Gly Lys Thr Thr Thr
                245                 250                 255

Ser Tyr Thr Thr Lys Ser Val Pro Thr Thr Tyr Val Phe Asp Phe Gly
            260                 265                 270

Lys Gly Ile Leu Asp Gln Ser Cys Gly Gly Val Phe Ser Asn Asn Gly
        275                 280                 285

Ser Ser Gln Val Gln Leu Arg Asp Val Val Leu Met Asn Gly Thr Val
    290                 295                 300
```

-continued

Val Tyr Asp Ser Asn Gly Ala Trp Asp Ser Ser Ala Leu Glu Glu Trp
305                 310                 315                 320

Leu Gln Arg Gln Lys Lys Val Ser Ile Glu Arg Ile Phe Glu Asn Ile
            325                 330                 335

Gly Pro Ser Ala Val Tyr Pro Ser Ile Leu Pro Gly Val Val Ile Ala
                340                 345                 350

Ser Pro Ser Gln Thr His Pro Asp Tyr Phe Tyr Gln Trp Ile Arg Asp
        355                 360                 365

Ser Ala Leu Thr Ile Asn Ser Ile Val Ser His Ser Ala Asp Pro Ala
    370                 375                 380

Ile Glu Thr Leu Leu Gln Tyr Leu Asn Val Ser Phe His Leu Gln Arg
385                 390                 395                 400

Thr Asn Asn Thr Leu Gly Ala Gly Ile Gly Tyr Thr Asn Asp Thr Val
            405                 410                 415

Ala Leu Gly Asp Pro Lys Trp Asn Val Asp Asn Thr Ala Phe Thr Glu
                420                 425                 430

Pro Trp Gly Arg Pro Gln Asn Asp Gly Pro Ala Leu Arg Ser Ile Ala
        435                 440                 445

Ile Leu Lys Ile Ile Asp Tyr Ile Lys Gln Ser Gly Thr Asp Leu Gly
    450                 455                 460

Ala Lys Tyr Pro Phe Gln Ser Thr Ala Asp Ile Phe Asp Asp Ile Val
465                 470                 475                 480

Arg Trp Asp Leu Arg Phe Ile Ile Asp His Trp Asn Ser Ser Gly Phe
            485                 490                 495

Asp Leu Trp Glu Glu Val Asn Gly Met His Phe Phe Thr Leu Leu Val
                500                 505                 510

Gln Leu Ser Ala Val Asp Arg Ser Leu Ser Tyr Phe Asn Ala Ser Glu
        515                 520                 525

Arg Ser Ser Pro Phe Val Glu Glu Leu Arg Gln Thr Arg Arg Asp Ile
    530                 535                 540

Ser Lys Phe Leu Val Asp Pro Ala Asn Gly Phe Ile Asn Gly Lys Tyr
545                 550                 555                 560

Asn Tyr Ile Val Glu Thr Pro Met Ile Ala Asp Thr Leu Arg Ser Gly
            565                 570                 575

Leu Asp Ile Ser Thr Leu Leu Ala Ala Asn Thr Val His Asp Ala Pro
                580                 585                 590

Ser Ala Ser His Leu Pro Phe Asp Ile Asn Asp Pro Ala Val Leu Asn
        595                 600                 605

Thr Leu His His Leu Met Leu His Met Arg Ser Ile Tyr Pro Ile Asn
    610                 615                 620

Asp Ser Ser Lys Asn Ala Thr Gly Ile Ala Leu Gly Arg Tyr Pro Glu
625                 630                 635                 640

Asp Val Tyr Asp Gly Tyr Gly Val Gly Glu Gly Asn Pro Trp Val Leu
            645                 650                 655

Ala Thr Cys Ala Ala Ser Thr Thr Leu Tyr Gln Leu Ile Tyr Arg His
                660                 665                 670

Ile Ser Glu Gln His Asp Leu Val Val Pro Met Asn Asn Asp Cys Ser
        675                 680                 685

Asn Ala Phe Trp Ser Glu Leu Val Phe Ser Asn Leu Thr Thr Leu Gly
    690                 695                 700

Asn Asp Glu Gly Tyr Leu Ile Leu Glu Phe Asn Thr Pro Ala Phe Asn
705                 710                 715                 720

Gln Thr Ile Gln Lys Ile Phe Gln Leu Ala Asp Ser Phe Leu Val Lys

```
                        725                 730                 735
Leu Lys Ala His Val Gly Thr Asp Gly Glu Leu Ser Glu Gln Phe Asn
            740                 745                 750

Lys Tyr Thr Gly Phe Met Gln Gly Ala Gln His Leu Thr Trp Ser Tyr
        755                 760                 765

Thr Ser Phe Trp Asp Ala Tyr Gln Ile Arg Gln Glu Val Leu Gln Ser
    770                 775                 780

Leu
785

<210> SEQ ID NO 29
<211> LENGTH: 20
<212> TYPE: PRT
<213> ORGANISM: Amorphotheca resinae
<220> FEATURE:
<221> NAME/KEY: MISC_FEATURE
<222> LOCATION: (1)..(20)
<223> OTHER INFORMATION: Amorphotheca resinae glucoamylase signal
      sequence

<400> SEQUENCE: 29

Met His Ser Phe Thr Ser Leu Leu Leu Val Ser Gly Leu Ala Leu Gln
1               5                   10                  15

Thr Ala Val Gly
            20

<210> SEQ ID NO 30
<211> LENGTH: 20
<212> TYPE: PRT
<213> ORGANISM: Corynascus sepedonium
<220> FEATURE:
<221> NAME/KEY: MISC_FEATURE
<222> LOCATION: (1)..(20)
<223> OTHER INFORMATION: Corynascus sepedonium glucoamylase signal
      sequence

<400> SEQUENCE: 30

Met His Ala Leu Ser Ser Leu Val Val Leu Gly Thr Cys Ala Val Gln
1               5                   10                  15

Thr Ala Leu Gly
            20

<210> SEQ ID NO 31
<211> LENGTH: 18
<212> TYPE: PRT
<213> ORGANISM: Aspergillus niger
<220> FEATURE:
<221> NAME/KEY: MISC_FEATURE
<222> LOCATION: (1)..(18)
<223> OTHER INFORMATION: Aspergillus niger glucoamylase signal sequence

<400> SEQUENCE: 31

Met Ser Phe Arg Ser Leu Leu Ala Leu Ser Gly Leu Val Cys Thr Gly
1               5                   10                  15

Leu Ala

<210> SEQ ID NO 32
<211> LENGTH: 20
<212> TYPE: PRT
<213> ORGANISM: Aspergillus niger
<220> FEATURE:
<221> NAME/KEY: MISC_FEATURE
<222> LOCATION: (1)..(20)
<223> OTHER INFORMATION: T. reesei glucoamylase signal sequence
```

```
<400> SEQUENCE: 32

Met His Val Leu Ser Thr Ala Val Leu Leu Gly Ser Val Ala Val Gln
1               5                   10                  15

Lys Val Leu Gly
            20

<210> SEQ ID NO 33
<211> LENGTH: 17
<212> TYPE: PRT
<213> ORGANISM: Botryotinia fuckeliana
<220> FEATURE:
<221> NAME/KEY: MISC_FEATURE
<222> LOCATION: (1)..(17)
<223> OTHER INFORMATION: Botryotinia fuckeliana glucoamylase signal
      sequence

<400> SEQUENCE: 33

Met Leu Trp Glu Arg Ala Thr Ala Phe Val Ala Gly Ala Leu Ser Ser
1               5                   10                  15

Ala

<210> SEQ ID NO 34
<211> LENGTH: 15
<212> TYPE: PRT
<213> ORGANISM: Auricularia delicata
<220> FEATURE:
<221> NAME/KEY: MISC_FEATURE
<222> LOCATION: (1)..(15)
<223> OTHER INFORMATION: Auricularia delicata glucoamylase signal
      sequence

<400> SEQUENCE: 34

Met Arg Leu Pro Ser Val Ala Phe Phe Ala Ala Ala Ala Ser Ala
1               5                   10                  15

<210> SEQ ID NO 35
<211> LENGTH: 20
<212> TYPE: PRT
<213> ORGANISM: Talaromyces stipitatus
<220> FEATURE:
<221> NAME/KEY: MISC_FEATURE
<222> LOCATION: (1)..(20)
<223> OTHER INFORMATION: Taloromyces stipitatus glucoamylase signal
      sequence

<400> SEQUENCE: 35

Met Thr Arg Leu Ser Ser Val Leu Cys Ala Leu Ala Ala Leu Gly Gln
1               5                   10                  15

Thr Ala Leu Ala
            20

<210> SEQ ID NO 36
<211> LENGTH: 20
<212> TYPE: PRT
<213> ORGANISM: Piriformospora indica
<220> FEATURE:
<221> NAME/KEY: MISC_FEATURE
<222> LOCATION: (1)..(20)
<223> OTHER INFORMATION: Piriformospora indica glucoamylase signal
      sequence

<400> SEQUENCE: 36

Met Leu Phe Thr Ser Val Phe Ser Cys Leu Leu Leu Ser Pro Gly
1               5                   10                  15

Gly Ala Leu Ala
            20
```

```
<210> SEQ ID NO 37
<211> LENGTH: 17
<212> TYPE: PRT
<213> ORGANISM: Punctularia strigosozonata
<220> FEATURE:
<221> NAME/KEY: MISC_FEATURE
<222> LOCATION: (1)..(17)
<223> OTHER INFORMATION: Punctularia strigosozonata glucoamylase signal
      sequence

<400> SEQUENCE: 37

Met Leu Ser Ser Leu Ile Val Ser Gly Leu Leu Ala Ser Gly Val Cys
1               5                   10                  15

Ala

<210> SEQ ID NO 38
<211> LENGTH: 18
<212> TYPE: PRT
<213> ORGANISM: Saccharomycopsis fibuligera - Sfib - 1.381
<220> FEATURE:
<221> NAME/KEY: MISC_FEATURE
<222> LOCATION: (1)..(18)
<223> OTHER INFORMATION: Saccharomycopsis fibuligera glucoamylase signal
      sequence

<400> SEQUENCE: 38

Met Ile Arg Leu Thr Val Phe Leu Thr Ala Val Phe Ala Ala Val Ala
1               5                   10                  15

Ser Cys

<210> SEQ ID NO 39
<211> LENGTH: 21
<212> TYPE: PRT
<213> ORGANISM: Saccharomyces cerevisiae
<220> FEATURE:
<221> NAME/KEY: MISC_FEATURE
<222> LOCATION: (1)..(21)
<223> OTHER INFORMATION: S. cerevisiae/diastaticus glucoamylase signal
      sequence

<400> SEQUENCE: 39

Met Gln Arg Pro Phe Leu Leu Ala Tyr Leu Val Leu Ser Leu Leu Phe
1               5                   10                  15

Asn Ser Ala Leu Gly
                20

<210> SEQ ID NO 40
<211> LENGTH: 18
<212> TYPE: PRT
<213> ORGANISM: Saccharomyces cerevisiae
<220> FEATURE:
<221> NAME/KEY: MISC_FEATURE
<222> LOCATION: (1)..(18)
<223> OTHER INFORMATION: S. cerevisiae AGA2 glucoamylase signal sequence

<400> SEQUENCE: 40

Met Gln Leu Leu Arg Cys Phe Ser Ile Phe Ser Val Ile Ala Ser Val
1               5                   10                  15

Leu Ala

<210> SEQ ID NO 41
<211> LENGTH: 19
<212> TYPE: PRT
<213> ORGANISM: Saccharomyces cerevisiae
<220> FEATURE:
```

```
<221> NAME/KEY: MISC_FEATURE
<222> LOCATION: (1)..(19)
<223> OTHER INFORMATION: S. cerevisiae EXG1 glucoamylase signal sequence

<400> SEQUENCE: 41

Met Leu Ser Leu Lys Thr Leu Leu Cys Thr Leu Leu Thr Val Ser Ser
1               5                   10                  15

Val Leu Ala

<210> SEQ ID NO 42
<211> LENGTH: 19
<212> TYPE: PRT
<213> ORGANISM: Saccharomyces cerevisiae
<220> FEATURE:
<221> NAME/KEY: MISC_FEATURE
<222> LOCATION: (1)..(19)
<223> OTHER INFORMATION: S. cerevisiae Mfalfa signal sequence

<400> SEQUENCE: 42

Met Arg Phe Pro Ser Ile Phe Thr Ala Val Leu Phe Ala Ala Ser Ser
1               5                   10                  15

Ala Leu Ala

<210> SEQ ID NO 43
<211> LENGTH: 44
<212> TYPE: PRT
<213> ORGANISM: Trichoderma reesei
<220> FEATURE:
<221> NAME/KEY: MISC_FEATURE
<222> LOCATION: (1)..(44)
<223> OTHER INFORMATION: T. reesei Xyn2 signal sequence

<400> SEQUENCE: 43

Met Val Ser Phe Thr Ser Leu Leu Ala Ala Ser Pro Pro Ser Arg Ala
1               5                   10                  15

Ser Cys Arg Pro Ala Ala Glu Val Glu Ser Val Ala Val Glu Lys Arg
                20                  25                  30

Gln Thr Ile Gln Pro Gly Thr Gly Tyr Asn Asn Gly
            35                  40

<210> SEQ ID NO 44
<211> LENGTH: 17
<212> TYPE: PRT
<213> ORGANISM: Aspergillus niger
<220> FEATURE:
<221> NAME/KEY: MISC_FEATURE
<222> LOCATION: (1)..(17)
<223> OTHER INFORMATION: S. cerevisiae/diastaticus glucoamylase signal
      sequence

<400> SEQUENCE: 44

Met Val Lys Ser Ile Leu Ala Ser Val Phe Phe Ala Ala Thr Ala Leu
1               5                   10                  15

Ala

<210> SEQ ID NO 45
<211> LENGTH: 70
<212> TYPE: DNA
<213> ORGANISM: Artificial Sequence
<220> FEATURE:
<223> OTHER INFORMATION: Primer DBC-16841

<400> SEQUENCE: 45
cttatcgata ccgtcgacct cgagggggggg cccggtaccc agcttttgtt gggccagaaa    60
```

-continued

| aaggaagtgt | 70 |

<210> SEQ ID NO 46
<211> LENGTH: 70
<212> TYPE: DNA
<213> ORGANISM: Artificial Sequence
<220> FEATURE:
<223> OTHER INFORMATION: Primer DBC-16903

<400> SEQUENCE: 46

| taatattgaa aaaggaagag tatgagtatt caacatttcc gtgtcgccct ggaggaaatg | 60 |
| agaaatgaga | 70 |

<210> SEQ ID NO 47
<211> LENGTH: 70
<212> TYPE: DNA
<213> ORGANISM: Artificial Sequence
<220> FEATURE:
<223> OTHER INFORMATION: Primer DBC-16904

<400> SEQUENCE: 47

| taatattgaa aaaggaagag tatgagtatt caacatttcc gtgtcgccct ggaggaaatg | 60 |
| agaaatgaga | 70 |

<210> SEQ ID NO 48
<211> LENGTH: 20
<212> TYPE: DNA
<213> ORGANISM: Artificial Sequence
<220> FEATURE:
<223> OTHER INFORMATION: Primer DBC-16844

<400> SEQUENCE: 48

| gaacaaaagc tgggtaccgg | 20 |

<210> SEQ ID NO 49
<211> LENGTH: 4967
<212> TYPE: DNA
<213> ORGANISM: Artificial Sequence
<220> FEATURE:
<223> OTHER INFORMATION: plasmid pRS313

<400> SEQUENCE: 49

| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataattc cgttttaaga gcttggtgag cgctaggagt cactgccagg tatcgtttga | 240 |
| acacggcatt agtcagggaa gtcataacac agtcctttcc cgcaatttc ttttctatt | 300 |
| actcttggcc tcctctagta cactctatat tttttatgc ctcggtaatg attttcattt | 360 |
| ttttttttcc acctagcgga tgactctttt tttttcttag cgattggcat tatcacataa | 420 |
| tgaattatac attatataaa gtaatgtgat ttcttcgaag aatatactaa aaaatgagca | 480 |
| ggcaagataa acgaaggcaa agatgacaga gcagaaagcc ctagtaaagc gtattacaaa | 540 |
| tgaaaccaag attcagattg cgatctcttt aaagggtggt ccctagcga tagagcactc | 600 |
| gatcttccca gaaaaagagg cagaagcagt agcagaacag gccacacaat cgcaagtgat | 660 |
| taacgtccac acaggtatag ggtttctgga ccatatgata catgctctgg ccaagcattc | 720 |
| cggctggtcg ctaatcgttg agtgcattgg tgacttacac atagcgacc atcacaccac | 780 |
| tgaagactgc gggattgctc tcggtcaagc ttttaaagag gccctactgg cgcgtggagt | 840 |

```
aaaaaggttt ggatcaggat ttgcgccttt ggatgaggca ctttccagag cggtggtaga    900
tctttcgaac aggccgtacg cagttgtcga acttggtttg caaagggaga agtaggaga     960 tctctcttgc gagatgatcc cgcattttct tgaaagcttt gcagaggcta gcagaattac   1020
cctccacgtt gattgtctgc gaggcaagaa tgatcatcac cgtagtgaga gtgcgttcaa   1080
ggctcttgcg gttgccataa gagaagccac ctcgcccaat ggtaccaacg atgttccctc   1140
caccaaaggt gttcttatgt agtgacaccg attatttaaa gctgcagcat acgatatata   1200
tacatgtgta tatatgtata cctatgaatg tcagtaagta tgtatacgaa cagtatgata   1260
ctgaagatga caaggtaatg catcattcta tacgtgtcat tctgaacgag gcgcgctttc   1320
cttttttctt tttgctttt cttttttttt ctcttgaact cgacggatca tatgcggtgt    1380
gaaataccgc acagatgcgt aaggagaaaa taccgcatca ggaaattgta acgttaata    1440 ttttgttaaa attcgcgtta aattttgtt aaatcagctc attttttaac caataggccg    1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt ttttgggt      1680 cgaggtgccg taaagcacta atcggaacc ctaaagggag ccccgatttt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa gggggatgt gctgcaaggc    1980 gattaagttg ggtaacgcca gggttttccc agtcacgacg ttgtaaaacg acggccagtg   2040
aattgtaata cgactcacta tagggcgaat tggagctcca ccgcggtggc ggccgctcta   2100
gaactagtgg atccccccggg ctgcaggaat tcgatatcaa gcttatcgat accgtcgacc   2160
tcgagggggg gcccggtacc cagcttttgt tccctttagt gagggttaat tccgagcttg   2220
gcgtaatcat ggtcatagct gtttcctgtg tgaaattgtt atccgctcac aattccacac   2280
aacataggag ccggaagcat aaagtgtaaa gcctggggtg cctaatgagt gaggtaactc   2340
acattaattg cgttgcgctc actgcccgct ttccagtcgg gaaacctgtc gtgccagctg   2400
cattaatgaa tcggccaacg cgcgggagga ggcggtttgc gtattgggcg ctcttccgct   2460
tcctcgctca ctgactcgct gcgctcggtc gttcggctgc ggcgagcggt atcagctcac   2520
tcaaaggcgg taatacggtt atccacagaa tcaggggata acgcaggaaa gaacatgtga   2580
gcaaaaggcc agcaaaggc caggaaccgt aaaaaggccg cgttgctggc gtttttccat    2640
aggctcggcc cccctgacga gcatcacaaa aatcgacgct caagtcagag gtggcgaaac   2700
ccgacaggac tataaagata ccaggcgttc cccctggaa gctccctcgt gcgctctcct    2760
gttccgaccc tgccgcttac cggatacctg tccgcctttc tcccttcggg aagcgtggcg   2820
ctttctcaat gctcacgctg taggtatctc agttcggtgt aggtcgttcg ctccaagctg   2880
ggctgtgtgc acgaaccccc cgttcagccc gaccgctgcg ccttatccgg taactatcgt   2940
cttgagtcca acccggtaag acacgactta tcgccactgg cagcagccac tggtaacagg   3000
attagcagag cgaggtatgt aggcggtgct acagagttct tgaagtggtg gcctaactac   3060
ggctacacta gaaggacagt atttggtatc tgcgctctgc tgaagccagt taccttcgga   3120
aaaagagttg gtagctcttg atccggcaaa caaaccaccg ctggtagcgg tggtttttt    3180
```

| | |
|---|---|
| gtttgcaagc agcagattac gcgcagaaaa aaaggatctc aagaagatcc tttgatcttt | 3240 |
| tctacggggt ctgacgctca gtggaacgaa aactcacgtt aagggatttt ggtcatgaga | 3300 |
| ttatcaaaaa ggatcttcac ctagatcctt ttaaattaaa aatgaagttt taaatcaatc | 3360 |
| taaagtatat atgagtaaac ttggtctgac agttaccaat gcttaatcag tgaggcacct | 3420 |
| atctcagcga tctgtctatt tcgttcatcc atagttgcct gactgcccgt cgtgtagata | 3480 |
| actacgatac gggagggctt accatctggc cccagtgctg caatgatacc gcgagaccca | 3540 |
| cgctcaccgg ctccagattt atcagcaata aaccagccag ccggaagggc cgagcgcaga | 3600 |
| agtggtcctg caactttatc cgcctccatc cagtctatta attgttgccg ggaagctaga | 3660 |
| gtaagtagtt cgccagttaa tagtttgcgc aacgttgttg ccattgctac aggcatcgtg | 3720 |
| gtgtcacgct cgtcgtttgg tatggcttca ttcagctccg gttcccaacg atcaaggcga | 3780 |
| gttacatgat cccccatgtt gtgaaaaaaa gcggttagct ccttcggtcc tccgatcgtt | 3840 |
| gtcagaagta agttggccgc agtgttatca ctcatggtta tggcagcact gcataattct | 3900 |
| cttactgtca tgccatccgt aagatgcttt tctgtgactg gtgagtactc aaccaagtca | 3960 |
| ttctgagaat agtgtatgcg gcgaccgagt tgctcttgcc cggcgtcaat acgggataat | 4020 |
| accgcgccac atagcagaac tttaaaagtg ctcatcattg gaaaacgttc ttcggggcga | 4080 |
| aaactctcaa ggatcttacc gctgttgaga tccagttcga tgtaacccac tcgtgcaccc | 4140 |
| aactgatctt cagcatcttt tactttcacc agcgtttctg ggtgagcaaa aacaggaagg | 4200 |
| caaaatgccg caaaaaaggg aataagggcg acacggaaat gttgaatact catactcttc | 4260 |
| cttttcaat attattgaag catttatcag ggttattgtc tcatgagcgg atacatattt | 4320 |
| gaatgtattt agaaaaataa acaaataggg gttccgcgca catttccccg aaaagtgcca | 4380 |
| cctgggtcct tttcatcacg tgctataaaa ataattataa tttaaatttt ttaatataaa | 4440 |
| tatataaatt aaaaatagaa agtaaaaaaa gaaattaaag aaaaaatagt ttttgttttc | 4500 |
| cgaagatgta aaagactcta gggggatcgc caacaaatac tacctttat cttgctcttc | 4560 |
| ctgctctcag gtattaatgc cgaattgttt catcttgtct gtgtagaaga ccacacacga | 4620 |
| aaatcctgtg attttacatt ttacttatcg ttaatcgaat gtatatctat ttaatctgct | 4680 |
| tttcttgtct aataaatata tatgtaaagt acgcttttg ttgaaatttt ttaaacctt | 4740 |
| gtttatttt ttttcttcat tccgtaactc ttctaccttc tttatttact ttctaaaatc | 4800 |
| caaatacaaa acataaaaat aaataaacac agagtaaatt cccaaattat tccatcatta | 4860 |
| aaagatacga ggcgcgtgta agttacaggc aagcgatccg tcctaagaaa ccattattat | 4920 |
| catgacatta acctataaaa ataggcgtat cacgaggccc tttcgtc | 4967 |

<210> SEQ ID NO 50
<211> LENGTH: 50
<212> TYPE: DNA
<213> ORGANISM: Artificial Sequence
<220> FEATURE:
<223> OTHER INFORMATION: connector sequence

<400> SEQUENCE: 50
tcctgtacgc actttgtccc acaaattccc gattccgcaa tttgttcgcc            50

<210> SEQ ID NO 51
<211> LENGTH: 50
<212> TYPE: DNA
<213> ORGANISM: Artificial Sequence
<220> FEATURE:
<223> OTHER INFORMATION: connector sequence

```
<400> SEQUENCE: 51
gaacaggata tttcgatctt ggatacgtac tcgcttgtgt ctggtttcgt                50

<210> SEQ ID NO 52
<211> LENGTH: 20
<212> TYPE: DNA
<213> ORGANISM: Artificial Sequence
<220> FEATURE:
<223> OTHER INFORMATION: integration target sequence

<400> SEQUENCE: 52
agaaaactct tagcttttcc                                                 20

<210> SEQ ID NO 53
<211> LENGTH: 20
<212> TYPE: DNA
<213> ORGANISM: Artificial Sequence
<220> FEATURE:
<223> OTHER INFORMATION: integration target sequence

<400> SEQUENCE: 53
caatatggta tgccgagtct                                                 20
```

YEAST CELLS FOR GLYCEROL FREE ETHANOL PRODUCTION

CROSS-REFERENCE TO RELATED APPLICATIONS

This application is a National Stage entry of International Application No. PCT/EP2018/075959, filed Sep. 25, 2018, which claims priority to European Patent Application No. 18191191.8, filed Aug. 28, 2018, and European Patent Application No. 17193915.0, filed Sep. 29, 2017.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-520000_ST25.txt" created on 28 Feb. 2020 and 132,874 bytes in size) is submitted concurrently with the instant application, and the entire contents of the Sequence Listing are incorporated herein by reference.

BACKGROUND

Field

The invention relates to a recombinant cell suitable for ethanol production, the use of this cell for the preparation of ethanol and/or succinic acid, and a process for preparing fermentation product using said recombinant cell.

DESCRIPTION OF RELATED ART

Ethanol production from starch-containing material is well-known in the art. As a first step, starch is usually converted into dextrins using an amylase. The dextrins are subsequentially hydrolyzed into D-glucose using glucoamylase. The glucose is fermented into ethanol. Amylase and glucoamylase are conventionally added to the starch media. Alternatively, yeast can be transformed with a glucoamylase gene. There is still room for improvement for recombinant yeasts having a glucoamylase gene.

TABLE 1

Short description of the sequences

| SEQ ID NO | Description |
|---|---|
| 1 | *K. pneumoniae* glycerol dehydrogenase |
| 2 | *E. aerogenes* glycerol dehydrogenase |
| 3 | *Y. aldovae* glycerol dehydrogenase |
| 4 | *K. pneumoniae* dihydroxyacetone kinase |
| 5 | *Y. lipolytica* dihydroxyacetone kinase |
| 6 | *S. pombe* dihydroxyacetone kinase |
| 7 | *D. rerio* aquaporin 9 |
| 8 | *Z. rouxii* T5 transporter |
| 9 | *E. coli* groES |
| 10 | *E. coli* groEL |
| 11 | *Thiobacillus denitrificans* RubisCO cbbM |
| 12 | *Spinacia* PRK |
| 13 | *E. coli* glycerol dehydrogenase |
| 14 | *S. cerevisiae* dihydroxyacetone kinase |
| 15 | PRK motif |
| 16 | PRK motif |
| 17 | *Punctularia strigosozonata* glucoamylase (mature) |
| 18 | *Punctularia strigosozonata* glucoamylase (mature) with native signal sequence |

TABLE 1-continued

Short description of the sequences

| SEQ ID NO | Description |
|---|---|
| 19 | *Amorphotheca resinae* glucoamylase (mature) |
| 20 | *Corynascus sepedonium* glucoamylase (mature) |
| 21 | *Aspergillus niger* glucoamylase (mature) |
| 22 | *T. reesei* glucoamylase (mature) |
| 23 | *Botryotinia fuckeliana* glucoamylase (mature) |
| 24 | *Auricularia delicata* Glucoamylase (mature) |
| 25 | *Talaromyces stipitatus* glucoamylase (mature) |
| 26 | *Piriformospora indica* glucoamylase (mature) |
| 27 | *Saccharomycopsis fibuligera* glucoamylase (mature) |
| 28 | *S. cerevisiae diastaticus* glucoamylase (mature) |
| 29 | *Amorphotheca resinae* glucoamylase signal sequence |
| 30 | *Corynascus sepedonium* glucoamylase signal sequence |
| 31 | *Aspergillus niger* glucoamylase signal sequence |
| 32 | *T. reesei* glucoamylase signal sequence |
| 33 | *Botryotinia fuckeliana* glucoamylase signal sequence |
| 34 | *Auricularia delicata* glucoamylase signal sequence |
| 35 | *Taloromyces stipitatus* glucoamylase signal sequence |
| 36 | *Piriformospora indica* glucoamylase signal sequence |
| 37 | *Punctularia strigosozonata* glucoamylase signal sequence |
| 38 | *Saccharomycopsis fibuligera* glucoamylase signal sequence |
| 39 | *S. cerevisiae/diastaticus* glucoamylase signal sequence |
| 40 | *S. cerevisiae* AGA2 glucoamylase signal sequence |
| 41 | *S. cerevisiae* EXG1 glucoamylase signal sequence |
| 42 | *S. cerevisiae* Mfalfa signal sequence |
| 43 | *T. reesei* Xyn2 signal sequence |
| 44 | *S. cerevisiae/diastaticus* glucoamylase signal sequence |
| 45 | Primer DBC-16841 |
| 46 | Primer DBC-16903 |
| 47 | Primer DBC-16904 |
| 48 | Primer DBC-16844 |
| 49 | plasmid pRS313 |
| 50 | connector sequence |
| 51 | connector sequence |
| 52 | integration target sequence |
| 53 | integration target sequence |

SUMMARY

The present invention relates to a recombinant yeast comprising: a nucleotide sequence allowing the expression of a glucoamylase having an amino acid sequence according to SEQ ID NO: 17 or which glucoamylase has an amino acid sequence which has a sequence identity of at least 70% of SEQ ID NO: 17.

DETAILED DESCRIPTION

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "gene" or "nucleotide sequence", this means "at least one" of that gene or nucleotide sequence, e.g. "at least one gene" or "at least one nucleotide sequence" unless specified otherwise. The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the cell, in particular a yeast cell, and usually corresponds to an oxygen consumption of less than 5 mmol/l·h$^{-1}$, in particular to an oxygen consumption of less than 2.5 mmol/l·h$^{-1}$, or less than 1 mmol/l·h$^{-1}$. More preferably 0 mmol/l/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant yeast" as used herein, refers to a yeast strain containing nucleic acid which is the result of one or more genetic modifications using recombinant DNA technique(s) and/or another mutagenic technique(s). In particular a recombinant yeast may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

In the context of this invention an "altered gene" has the same meaning as a mutated gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. "SEQ ID NO: X"), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE.

For the purpose of this invention the NEEDLE program from the EMBOSS package was used (version 2.8.0 or higher, EMBOSS: The European Molecular Biology Open Software Suite (2000) Rice,P. Longden,I. and Bleasby,A. Trends in Genetics 16, (6) pp276-277, emboss.bioinformatics.nl). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "disruption" is meant (or includes) all nucleic acid modifications such as nucleotide deletions or substitutions, gene knock-outs, (other) which affect the translation or transcription of the corresponding polypeptide and/or which affect the enzymatic (specific) activity, its substrate specificity, and/or or stability. Such modifications may be targeted on the coding sequence or on the promoter of the gene.

In one aspect the invention provides a recombinant yeast cell comprising a nucleotide sequence allowing the expression of a glucoamylase having an amino acid sequence according to SEQ ID NO: 17 or which glucoamylase has an amino acid sequence which has a sequence identity of at least 70% of SEQ ID NO: 17, preferably at least 75%, 80%, 85%, 90%, 95, 98%, or 99%.

Glucoamylase (EC 3.2.1.20 or 3.2.1.3), also referred to as amyloglucosidase, alpha-glucosidase, glucan 1,4-alpha glucosidase, maltase glucoamylase, and maltase-glucoamylase, catalyses at least the hydrolysis of terminal 1,4-linked alpha-D-glucose residues from non-reducing ends of amylose chains to release free D-glucose.

The polypeptide of SEQ ID NO: 17 encodes a "mature glucoamylase", referring to the enzyme in its final form after translation and any post-translational modifications, such as N-terminal processing, C-terminal truncation, glycosylation, phosphorylation, etc.

In an embodiment the nucleotide sequence allowing the expression of a glucoamylase encodes a polypeptide having an amino acid sequence of SEQ ID NO: 18 or a variant thereof having a sequence identity of at least 50%, preferably at least 60%, 70%, 75%, 80%, 85%, 90%, 95, 98%, or 99%. Amino acids 1-17 of the SEQ ID NO: 18 may encode for a signal sequence.

A signal sequence (also referred to as signal peptide, targeting signal, localization signal, localization sequence, transit peptide, leader sequence or leader peptide) can be present at the N-terminus of a polypeptide (here, the glucoamylase) where it signals that the polypeptide is to be excreted, for example outside the cell and into the media.

The inventors have found that a glucoamylase of SEQ ID NO: 17 or a functional homologue thereof provides a better yeast than with other glucoamylases. For example, the glucoamylase of SEQ ID NO: 17 or a functional homologues thereof may have beneficial side activities, or increased side activities such as pullananase activity. Also, the yeast may be more robust.

In another embodiment the nucleotide sequence allowing the expression of a glucoamylase encodes a polypeptide having an amino acid sequence of SEQ ID NO: 19 or a variant thereof having a sequence identity of at least 50%, preferably at least 60%, 70%, 75%, 80%, 85%, 90%, 95, 98%, or 99%. Amino acids 1-19 of the SEQ ID NO: 19 may encode for a signal sequence.

In an embodiment the recombinant yeast further comprises a nucleotide sequence coding for a glycerol dehydrogenase.

In an embodiment the glycerol dehydrogenase is a NAD linked glycerol dehydrogenase (EC 1.1.1.6). Such enzyme may be from bacterial origin or for instance from fungal origin. An example is gldA from *E. coli*.

Alternatively, the enzyme having glycerol dehydrogenase activity is a NADP$^+$ linked glycerol dehydrogenase (EC 1.1.1.72).

When the recombinant yeast is used for ethanol production, which typically takes place under anaerobic conditions, NAD linked glycerol dehydrogenase are preferred.

In an embodiment the recombinant yeast comprises one or more nucleotide sequences encoding a heterologous glycerol dehydrogenase represented by amino acid sequence SEQ ID NO: 1, 2, 3 or 13 or a functional homologue thereof a having sequence identity of at least 50%, preferably at least 60%, 70%, 75%, 80% 85%, 90%, 95%, 98% or 99%.

It is understood that the recombinant yeast has an endogenous nucleotide sequence coding a dihydroxy acetone kinase, such as a DAK1 gene. Such nucleotide sequence is preferably placed under control of a constitutive promoter. In an embodiment the recombinant yeast comprises one or more nucleic acid sequences encoding a dihydroxy acetone kinase represented by amino acid sequence according to SEQ ID NO: 4, 5, 6, or 14 or by a functional homologue thereof having a sequence identity of at least 50%, preferably at least 60%, 70%, 75%, 80%, 85%, 90%, 95, 98%, or 99%, which nucleotide sequence is preferably placed under control of a constitutive promoter. The dihydroxy acetone kinase may also have glyceraldehyde kinase activity.

In an embodiment the recombinant yeast comprises a nucleotide sequence coding for a glycerol transporter. In this embodiment any glycerol that is externally available in the medium (e.g. from the backset in corn mash) or secreted after internal cellular synthesis may be transported into the cell and converted to ethanol. In an embodiment the recombinant yeast comprises one or more nucleic acid sequences encoding a heterologous glycerol transporter represented by amino acid sequence SEQ ID NO:7 or a functional homologue thereof having a sequence identity of at least 50%, preferably at least 60%, 70%, 75%, 80%, 85%, 90%, 95%, 98%, or 99%.

In an embodiment the recombinant yeast further comprises a deletion or disruption of one or more endogenous nucleotide sequences encoding a glycerol exporter (e.g FPS1). In an embodiment the recombinant yeast comprises one or more nucleic acid sequences encoding a heterologous glycerol transporter represented by amino acid sequence SEQ ID NO: 8 or a functional homologue thereof having a sequence identity of at least 50%, preferably at least 60%, 70%, 75%, 80% 85%, 90%, 95%, 98% or 99%.

In another embodiment the recombinant yeast further comprises a deletion or disruption of one or more endogenous nucleotide sequences encoding a glycerol kinase (EC 2.7.1.30). An example of such an enzyme is Gut1p.

In a further embodiment, the recombinant yeast naturally lacks enzymatic activity needed for the NADH-dependent glycerol synthesis or has reduced enzymatic activity needed for NADH-dependent glycerol synthesis compared to its corresponding wild type yeast, for example yeast belonging to the species *Brettanomyces intermedius*.

In an embodiment the recombinant yeast comprises a deletion or disruption of one or more endogenous nucleotide sequences encoding a glycerol 3-phosphate phosphohydrolase and/or encoding a glycerol-3-phosphate dehydrogenase. Such a deletion or disruption may result in decrease or removal of enzymatic activity. A deleted or disrupted glycerol-3-phosphate dehydrogenase preferably may belong to EC 1.1.5.3, such as GUT2, or to EC 1.1.1.8, such as PDP1 and or PDP2.

In an embodiment the recombinant yeast is free of nucleotide sequences encoding NADH-dependent glycerol-3-phosphate dehydrogenase.

A reduced enzymatic activity can be achieved by modifying one or more nucleotide sequences encoding a NAD-dependent glycerol 3-phosphate dehydrogenase activity (GPD) or one or more nucleotide sequences encoding a glycerol phosphate phosphatase activity (GPP), such that the enzyme is expressed considerably less than in the wild-type or such that the nucleotide sequence encodes a polypeptide with reduced activity. Such modifications can be carried out using commonly known biotechnological techniques, and may in particular include one or more knock-out mutations or site-directed mutagenesis of promoter regions or coding regions of the structural genes encoding GPD and/or GPP. Alternatively, strains that are defective in glycerol production may be obtained by random mutagenesis followed by selection of strains with reduced or absent activity of GPD and/or GPP. Examples of genes in *S. cerevisiae* encoding GPD-activity are GPD1, GPD2, and GPP-activity are GPP1 and GPP2.

GPD and/or GPP may be entirely deleted, or at least a part is deleted which encodes a part of the enzyme that is essential for its activity. In particular, good results have been achieved with a *S. cerevisiae* cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in *Saccharomyces cerevisiae* by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization.

In an embodiment the recombinant yeast further comprises:
 a nucleotide sequence coding for a ribulose-1,5-biphosphate carboxylase oxygenase (EC 4.1.1.39, RuBisCO); and
 a nucleotide sequence coding for a phosphoribulokinase (EC 2.7.1.19, PRK);

The Rubisco may be a single-subunit Rubisco or a Rubisco having more than one subunit. In particular, good results have been achieved with a single-subunit Rubisco. In particular, good results have been achieved with a form-II Rubisco, more in particular CbbM. SEQ ID NO: 11 shows a suitable sequence of a suitable Rubisco. It is encoded by the cbbM gene from *Thiobacillus denitrificans*. An alternative to this Rubisco is a functional homologue of this Rubisco, in particular such functional homologue comprising an amino acid sequence having at least 80%, 85%, 90% or 95% sequence identity with SEQ ID NO: 11. Suitable natural Rubisco polypeptides are given in Table 1 of WO2014/129898. The Rubisco is preferably functionally expressed in the microorganism, at least during use in an industrial process for preparing a compound of interest.

In an embodiment the functionally expressed Rubisco has an activity, defined by the rate of ribulose-1,5-bisphosphate-dependent $^{14}C$-bicarbonate incorporation by cell extracts of at least 1 nmol·min$^{-1}$·(mg protein)$^{-1}$, in particular an activity of at least 2 nmol·min$^{-1}$·(mg protein)$^{-1}$, more in particular an activity of at least 4 nmol·min$^{-1}$·(mg protein)$^{-1}$. The upper limit for the activity is not critical. In practice, the activity may be about 200 nmol·min$^{-1}$·(mg protein)$^{-1}$ or less, in particular 25 nmol·min$^{-1}$·(mg protein)$^{-1}$, more in particular 15 nmol·min$^{-1}$·(mg protein)$^{-1}$ or less, e.g. about 10 nmol·min$^{-1}$·(mg protein)$^{-1}$ or less. The conditions for an assay for determining this Rubisco activity are as found in Example 4 of WO2014/129898.

In an embodiment the recombinant yeast further comprises one or more nucleotide sequences, preferably a heterologous nucleotide sequences, coding for molecular chaperones, said chaperones preferably originating from a prokaryote, more preferably a bacterium, even more preferably *E. coli*.

Chaperones—when expressed—are preferably capable of functionally interacting with an enzyme in the microorganism, in particular with at least one of Rubisco and PRK. Chaperones are proteins that provide favourable conditions for the correct folding of other proteins, thus preventing aggregation. Newly made proteins usually must fold from a linear chain of amino acids into a three-dimensional form. Chaperonins belong to a large class of molecules that assist protein folding, called molecular chaperones. The energy to fold proteins is supplied by adenosine triphosphate (ATP). A review article about chaperones that is useful herein is written by Yebenes (2001); "Chaperonins: two rings for folding"; Hugo Yebenes et al. Trends in Biochemical Sciences, August 2011, Vol. 36, No. 8.

In an embodiment, the one or more chaperone is from a bacterium, more preferably from *Escherichia*, in particular *E. coli* GroEL and GroES from *E. coli* may in particular encoded in a microorganism according to the invention. Other preferred chaperones are chaperones from *Saccharomyces*, in particular *Saccharomyces cerevisiae* Hsp10 and Hsp60. If the chaperones are naturally expressed in an organelle such as a mitochondrion (examples are Hsp60 and Hsp10 of *Saccharomyces cerevisiae*) relocation to the cytosol can be achieved e.g. by modifying the native signal sequence of the chaperonins.

In eukaryotes the proteins Hsp60 and Hsp10 are structurally and functionally nearly identical to GroEL and GroES, respectively. Thus, it is contemplated that Hsp60 and Hsp10 from any eukaryotic cell may serve as a chaperone for the Rubisco. See Zeilstra-Ryalls J, Fayet O, Georgopoulos C (1991). "The universally conserved GroE (Hsp60) chaperonins". Annu Rev Microbiol. 45: 301-25. doi:10.1146/annurev.mi.45.100191.001505. PMID 1683763 and Horwich A L, Fenton W A, Chapman E, Farr G W (2007). "Two Families of Chaperonin: Physiology and Mechanism". Annu Rev Cell Dev Biol. 23: 115-45. doi:10.1146/annurev.cellbio.23.090506.123555. PMID 17489689.

As an alternative to GroEL a functional homologue of GroEL may be present, in particular a functional homologue comprising an amino acid sequence having at least 70%, 75%, 80%, 85%, 90% or 95% sequence identity with SEQ ID NO: 10. Suitable natural chaperones polypeptides homologous to SEQ ID NO: 10 are given in Table 4 of WO2014/129898.

As an alternative to GroES a functional homologue of GroES may be present, in particular a functional homologue comprising an amino acid sequence having at least 70%, 75%, 80%, 85%, 90% or 95% sequence identity with SEQ ID NO: 9. Suitable natural chaperones polypeptides homologous to SEQ ID NO: 9 are given in Table 3 of WO2014/129898.

In an embodiment, a 10 kDa chaperone from Table 3 of WO2014/129898 is combined with a matching 60 kDa chaperone from Table 4 from WO2014/129898 of the same organism genus or species for expression in the host. For instance: >gi|189189366|ref|XP_001931022.1|:71-168 10 kDa chaperonin [*Pyrenophora tritici-repentis*] expressed together with matching >gi|189190432|ref|XP_001931555.1| heat shock protein 60, mitochondrial precursor [*Pyrenophora tritici-repentis* Pt-1C-BFP].

All other combinations from Table 3 and 4 of WO2014/129898 similarly made with same organism source are also available to the skilled person for expression.

In an embodiment the PRK is originating from a plant selected from Caryophyllales, in particular from Amaranthaceae, in particular from *Spinacia*.

In an embodiment the recombinant yeast comprises one or more nucleic acid sequences encoding a PRK represented by amino acid sequence represented by SEQ ID NO: 12 or by a functional homologue thereof having sequence identity of at least 50%, preferably at least 60%, 70%, 75%, 80% 85%, 90%, 95%, 98%, or 99%.

A functionally expressed phosphoribulokinase (PRK, EC 2.7.1.19) is capable of catalysing the chemical reaction:

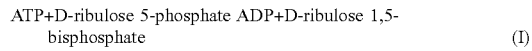

ATP+D-ribulose 5-phosphate ADP+D-ribulose 1,5-bisphosphate  (I)

Thus, the two substrates of this enzyme are ATP and D-ribulose 5-phosphate, whereas its two products are ADP and D-ribulose 1,5-bisphosphate.

PRK belongs to the family of transferases, specifically those transferring phosphorus-containing groups (phosphotransferases) with an alcohol group as acceptor. The systematic name of this enzyme class is ATP:D-ribulose-5-phosphate 1-phosphotransferase. Other names in common use include phosphopentokinase, ribulose-5-phosphate kinase, phosphopentokinase, phosphoribulokinase (phosphorylating), 5-phosphoribulose kinase, ribulose phosphate kinase, PKK, PRuK, and PRK. This enzyme participates in carbon fixation.

The PRK can be from a prokaryote or a eukaryote. Good results have been achieved with a PRK originating from a eukaryote. Preferably the eukaryotic PRK originates from a plant selected from Caryophyllales, in particular from Amaranthaceae, more in particular from *Spinacia*.

As an alternative to PRK from *Spinacia* a functional homologue of PRK from *Spinacia* may be present, in particular a functional homologue comprising a sequence having at least 70%, 75%, 80%. 85%, 90% or 95% sequence identity with the PRK from *Spinacia*.

The one or more PRK nucleotide sequences may be under the control of a promoter (the "PRK promoter") that enables higher expression under anaerobic conditions than under aerobic conditions.

In an embodiment the PRK promoter is ROX1 repressed. ROX1 is herein haeme-dependent repressor of hypoxic gene(s); that mediates aerobic transcriptional repression of hypoxia induced genes such as COX5b and CYC7; the repressor function is regulated through decreased promoter occupancy in response to oxidative stress; and contains an HMG domain that is responsible for DNA bending activity; involved in the hyperosmotic stress resistance. ROX1 is regulated by oxygen.

According to Kwast et al. (in: Genomic Analysis of Anaerobically induced genes in *Saccharomyces cerevisiae*: Functional roles of ROX1 and other factors in mediating the anoxic response, 2002, Journal of bacteriology vol 184, no 1 p 250-265): "*Although Rox1 functions in an O2-independent manner, its expression is oxygen (haeme) dependent, activated by the haeme-dependent transcription factor Hap1* [Keng, T. 1992. HAP1 and ROX1 form a regulatory pathway in the repression of HEM13 transcription in Saccharomyces cerevisiae. Mol. Cell. Biol. 12: 2616-2623]. *Thus, as oxygen levels fall to those that limit haeme biosynthesis* [Labbe-Bois, R., and P. Labbe. 1990. Tetrapyrrole and heme biosynthesis in the yeast Saccharomyces cerevisiae, p. 235-285. In H. A. Dailey (ed.), Biosynthesis of heme and chlorophylls. McGraw-Hill, N.Y., N. Y], ROX1 is no longer transcribed [Zitomer, R. S., and C. V. Lowry. 1992. Regulation of gene expression by oxygen in Saccharomyces cerevisiae. Microbiol. Rev. 56:1-11], *its protein levels fall* [Zitomer, R. S., P. Carrico, and J. Deckert. 1997. Regulation of hypoxic gene expression in yeast. Kidney Int 51:507-513], *and the genes it regulates are de-repressed.*"

In an embodiment, the PRK promoter is ROX1-repressed. In an embodiment, the PRK promoter has one or more ROX1 binding motif.

In an embodiment, the PRK promoter comprises in its sequence one or more of the motif according to SEQ ID NO: 15.

In an embodiment, the PRK promoter is the native promoter of a nucleotide sequence selected from the list consisting of: FET4, ANB1, YHR048W, DAN1, AAC3, TIR2, DIPS, HEM13, YNR014W, YAR028W, FUN 57, COX5B, OYE2, SUR2, FRDS1, PIS1, LAC1, YGRO35C, YAL028W, EUG1, HEM14, ISU2, ERG26, YMR252C and SML1, in particular FET4, ANB1, YHR048W, DAN1, AAC3, TIR2, DIPS and HEM13.

In an embodiment, the PRK promoter comprises in its sequence one or more of the motif according to TCGTTYAG and/or according to SEQ ID NO: 16.

In particular such PRK promoter is native promoter of a DAN, TIR or PAU gene. In an embodiment, the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W, YOR394W, YHL046C, YMR325W, YAL068C, YPL282C, PAU2, PAU4, in particular the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W.

In an embodiment, the promoter has a PRK expression ratio anaerobic/aerobic of 2 or more, 3 or more, 4 or more, 5 or more, 6 or more, 7 or more, 8 or more, 9 or more, 10 or more, 20 or more or 50 or more.

As used herein "promoter" is a DNA sequence that directs the transcription of a (structural) gene, herein in particular one or more phosphoribulokinase gene. The promoter enables higher expression during anaerobic conditions than under aerobic conditions.

In an embodiment, the PRK promoter may be a synthetic oligonucleotide. It may be a product of artificial oligonucleotide synthesis. Artificial oligonucleotide synthesis is a method in synthetic biology that is used to create artificial oligonucleotides, such as genes, in the laboratory. Commercial gene synthesis services are now available from numerous companies worldwide, some of which have built their business model around this task. Current gene synthesis approaches are most often based on a combination of organic chemistry and molecular biological techniques and entire genes may be synthesized "de novo", without the need for precursor template DNA.

In an embodiment, the promoter is located in the 5' region of a the PRK gene, In an embodiment it is located proximal to the transcriptional start site of PRK gene.

The PRK promoter may have a PRK expression ratio anaerobic/aerobic of 2 or more, 3 or more, 4 or more, 5 or more, 6 or more, 7 or more, 8 or more, 9 or more, 10 or more, 20 or more or 50 or more.

In an embodiment the PRK promoter is a synthetic oligonucleotide. The PRK promoter preferably enables expression only during anaerobic conditions.

A suitable PRK promoter is ANB1 and/or DAN1 as mentioned in EP16174382.8.

The recombinant yeast may contain genes of a pentose metabolic pathway non-native to the cell and/or that allow the recombinant cell to convert pentose(s). In one embodiment, the recombinant yeast may comprise one or two or more copies of one or more xylose isomerases and/or one or two or more copies of one or more xylose reductase and xylitol dehydrogenase genes, allowing the recombinant yeast convert xylose. In an embodiment thereof, these genes may be integrated into the recombinant cell genome. In another embodiment, the recombinant yeast comprises the genes araA, araB and araD. It is then able to ferment arabinose. In one embodiment the recombinant yeast comprises xylA-gene, XYL1 gene and XYL2 gene and/or XKS1-gene, to allow the recombinant yeast to ferment xylose; deletion of the aldose reductase (GRE3) gene; overexpression of one or more PPP-genes, e.g. TAL1, TAL2, TKL1, TKL2, RPE1 and RKI1 to allow the increase of the flux through the pentose phosphate path-way in the cell, and/or overexpression of GAL2 and/or deletion of GAL80. Thus though inclusion of the above genes, suitable pentose or other metabolic pathway(s) may be introduced in the recombinant yeast that were non-native in the (wild type) recombinant yeast.

In an embodiment the recombinant yeast comprises:
a nucleotide sequence coding for a glycerol dehydrogenase, a nucleotide sequence coding for a ribulose-1,5-biphosphate carboxylase oxygenase (EC 4.1.1.39);

a nucleotide sequence coding for a phosphoribulokinasey (EC 2.7.1.19);

a nucleotide sequence coding for a glucoamylase (EC 3.2.1.20 or 3.2.1.3); and a nucleotide sequence coding for a glycerol transporter.

In an embodiment, the following genes may be introduced in the recombinant yeast by introduction into a host cell:
1) a set consisting of PPP-genes TAL1, TKL1, RPE1 and RKI1, optionally under control of strong constitutive promoter;
2) a set consisting of a xylA-gene under control of strong constitutive promoter;
3) a set comprising a XKS1-gene under control of strong constitutive promoter,
4) a set consisting of the bacterial genes araA, araB and araD under control of a strong constitutive promoter,
5) deletion of an aldose reductase gene The above cells may be constructed using known recombinant expression techniques. The co-factor modification may be effected before, simultaneous or after any of the modifications 1-5 above.

The recombinant yeast may be selected from Saccharomycetaceae, in particular from the group of *Saccharomyces*, such as *Saccharomyces cerevisiae*; *Kluyveromyces*, such as *Kluyveromyces marxianus*; *Pichia*, such as *Pichia stipitis* or *Pichia angusta*; *Zygosaccharomyces*, such as *Zygosaccharomyces bailii*; and *Brettanomyces*, such as *Brettanomyces intermedius*, *Issatchenkia*, such as *Issatchenkia orientalis* and *Hansenula*.

The recombinant yeast may be subjected to evolutionary engineering to improve its properties. Evolutionary engineering processes are known processes. Evolutionary engineering is a process wherein industrially relevant phenotypes of a microorganism, herein the recombinant yeast, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008041840 and WO2009112472. After the evolutionary engineering the resulting pentose fermenting recombinant cell is isolated. The isolation may be executed in any known manner, e.g. by separation of cells from a recombinant cell broth used in the evolutionary engineering, for instance by taking a cell sample or by filtration or centrifugation.

In an embodiment, the recombinant yeast is marker-free. As used herein, the term "marker" refers to a gene encoding a trait or a phenotype which permits the selection of, or the screening for, a host cell containing the marker. Marker-free means that markers are essentially absent in the recombinant yeast. Being marker-free is particularly advantageous when antibiotic markers have been used in construction of the recombinant yeast and are removed thereafter. Removal of markers may be done using any suitable prior art technique, e.g. intramolecular recombination.

In one embodiment, the recombinant yeast is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

To increase the likelihood that enzyme activity is expressed at sufficient levels and in active form in the recombinant yeast, the nucleotide sequence encoding these enzymes, as well as the Rubisco enzyme and other enzymes of the disclosure are preferably adapted to optimise their codon usage to that of the recombinant yeast in question.

The adaptiveness of a nucleotide sequence encoding an enzyme to the codon usage of a cell may be expressed as codon adaptation index (CAI). The codon adaptation index is herein defined as a measurement of the relative adaptiveness of the codon usage of a gene towards the codon usage of highly expressed genes in a particular cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the host cell in question such as e.g. *S. cerevisiae* cells.

The invention further provides the use of a recombinant yeast according to the invention for preparation of ethanol.

The present invention also provides a process to produce ethanol comprising:
fermenting a composition comprising a fermentable carbohydrate, in particular selected from the group of glucose, fructose, sucrose, maltose, xylose, arabinose, galactose and mannose under anaerobic conditions in the presence of a recombinant yeast according to the invention; and
recovering the ethanol.

In an embodiment one such composition is a biomass hydrolysate. Such biomass hydrolysate may be a lignocellulosic biomass hydrolysate. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

In another embodiment such composition is a pre-treated cornstover hydrolysate. Another preferred composition is a corn fiber hydrolysate, which is optionally pre-treated.

In yet another embodiment such composition is a starch hydrolysate, such as a corn starch hydrolysate.

In the context of the invention a "hydrolysate" means a polysaccharide that has been depolymerized through the addition of water to form mono and oligosaccharide sugars. Hydrolysates may be produced by enzymatic or acid hydrolysis of the polysaccharide-containing material.

In an embodiment the fermentable carbohydrate is obtained from starch, lignocellulose, and/or pectin.

The starch, lignocellulose, and/or pectin may be contacted with an enzyme composition, wherein one or more sugar is produced, and wherein the produced sugar is fermented to give a fermentation product, wherein the fermentation is conducted with a recombinant yeast of the invention.

The process is particularly useful when glycerol is fed externally to the process, which is then taken up and converted to ethanol by the claimed recombinant yeast.

In an embodiment the composition comprises an amount of undissociated acetic acid of 10 mM or less.

The inventors have found that a recombinant yeast of the invention, specifically a S. cerevisiae cell is particularly sensitive towards acetic acid, as compared to non-recombinant cells. They have surprisingly found that the ethanol yield rapidly decreases when the composition contains more than 10 mM undissociated acetic acid, and that in order to avoid or lessen the negative effect of acetic acid the process should be performed with a composition having an amount of undissociated acetic acid of 10 mM or less, preferably 9 mM or less, 8 mM or less, 7 mM or less, 6 mM or less, 5 mM or less, 4 mM or less, 3 mM or less, 2 mM or less, 1 mM or less.

In an embodiment the composition has an initial undissociated acetic acid of 10 mM or less. In another embodiment, the amount of undissociated acetic acid is 10 mM or less throughout the process.

The lower amount of undissociated acetic acid is less important. In one embodiment, the composition is free of undissociated acetic acid.

In an embodiment, the lower limit of the amount of undissociated acetic acid is 50 µM or more, 55 µM or more, 60 µM or more, 70 µM or more, 80 µM or more, 90 µM or more, 100 µM or more.

The skilled person appreciates that the amount of undissociated acetic acid depends inter alia on the total amount of acetic acid in the composition (protonated and dissociated) as well on the pH.

In one embodiment the amount of undissociated acetic acid is maintained at a value of at 10 mM by adjusting the pH, e.g. by adding a base.

The process may comprise the step of monitoring the pH. The pH of the composition is preferably kept between 4.2 and 5.2, preferably between 4.5 and 5.0. The lower pH is preferably such that the amount of undissociated acetic acid is 10 mM or less, which inter alia depends on the total amount of acetic acid in the composition.

The skilled person knows how to provide or select a composition having an amount of undissociated acetic acid 10 mM or less. For example, he/she may measure the amount of undissociated acetic acid in a composition and select only those compositions which have an amount of undissociated acetic acid of 10 mM or less.

Alternatively, if the amount of undissociated acetic acid in a composition exceeds 10 mM, the process may comprise, prior to the fermentation step, adding a base (such as NaOH or KOH) until the amount of undissociated acetic acid in a composition has reached a value of 10 mM or less.

The amount of undissociated acetic acid may be analysed by HPLC. HPLC generally measures all acetic acid (i.e. both undissociated, i.e. protonated form and dissociated form of acetic acid) because the mobile phase is typically acidified. In order to measure the amount of undissociated acetic acid in the composition, a suitable approach is to measure the (total) amount of acetic acid of the composition as-is, measure the pH of the composition, and calculate the amount of undissociated acetic acid using the pKa of acetic acid.

In an embodiment the process of the invention comprises dosing glucoamylase at a concentration of 0.05 g/L or less, expressed as the total amount of glucoamylase enzyme in grams per liter of corn slurry.

The term "dosing" is understood to mean adding GA other than, or in addition to any GA which may be added via the yeast functionally expressing glucoamylase.

The amount of glucoamylase can be determined for example by proteomics, or by Western Blot. These techniques are known in the art. Glucoamylase may be dosed at a concentration between 0.04 g/L or less, or 0.03 g/L or less, or 0.02 g/L or less, or 0.01 g/L or less, or 0.005 g/L or less. In an embodiment glucoamylase is dosed at a concentration between 0 and 0.08 g/kg (i.e. between no GA and 0.08 g/kg), or between 0 and 0.04 g/kg, between 0 and 0.02 g/kg In an embodiment glucoamylase is dosed at a concentration between 0.005 and 0.05 g/L, between 0.01 and 0.05 g/L, between 0.02 and 0.05 g/L, between 0.03 and 0.05 g/L, or between 0.04 and 0.05 g/L. In an embodiment glucoamylase is dosed at concentration between 0.005 and 0.04 g/L, between 0.01 and 0.04 g/L, between 0.02 and 0.04 g/L, or between 0.03 and 0.04 g/L. In an embodiment glucoamylase is dosed at concentration between 0.005 and 0.04 g/L, between 0.005 and 0.03 g/L, between 0.005 and 0.02 g/L, or between 0.005 and 0.01 g/L.

In an embodiment the process of the invention is carried out without adding any glucoamylase.

The skilled person knows how to dose GA. GA may be dosed to the fermentation. GA can be dosed separately, before or after adding yeast. GA can be dosed as a dry product, e.g. as powder or a granulate, or as a liquid. GA can be dosed together with other components such as antibiotics. GA can also be dosed as part of the back set, i.e. a stream in which part of the thin stillage is recycled e.g. to the fermentation. GA can also be dosed using a combination of these methods.

EXAMPLES

Example 1

This Example relates to the performance of *Saccharomyces cerevisiae* strains transformed with glucoamylases from eleven different sources:

*Amorphotheca resinae* strain DAOM194228

*Corynascus sepedonium* ATCC9787

*Aspergillus niger*

*Trichoderma reesei*

*Botryotinia fuckeliana* BcDW1

*Auricularia delicata* TFB-10046 SS5

*Talaromyces stipitatus* ATCC 10500

*Piriformospora indica* DSM 11827

*Punctularia strigosozonata* HHB-11173 SS5

*Saccharomycopsis fibuligera*

*Saccharomyces diastaticus*

The strains were made using Ethanol Red as starting strain. Ethanol Red is a commercial *Saccharomyces cerevisiae* strain, available from Lesaffre. A HIS 3 deletion was made in Ethanol Red by deleting the entire ORF.

Each GA was placed behind its native leader as well as the *Saccharomyces cerevisiae* alpha mating signal (Sc_Mfalfa.sig) according to Table 1. All expression cassettes were ordered as promoter-ORF-terminator cassette at DNA2.0. All signal sequence-mature ORF combinations are downstream of the Sc_PGK1 promoter and upstream of the Sc_ENO1 terminator.

All expression cassettes were amplified with 50 bp-homology to pRS313 (single copy vector with HIS3 marker). The pRS313 plasmid was amplified as well. For DNA amplifications, Phusion High-Fidelity DNA Polymerase (New England Biolabs) was used according to the manufacturer's instructions. DNA amplifications were carried out using 4 ng of template and a Tm of 60° C. Primer concentrations ranged from 0.5 µM for regular primers to 0.05 µM for longer primers (>500). To remove possible contaminants and residual primers, the reactions were purified using the NucleoSpin96 PCR Clean-up Kit. The pRS313 plasmid with the GA expression cassette was assembled in vivo.

Performance of GAs was tested in two stages. Firstly, strains were tested for micro-aerobic growth in microtiter plate. Eight single colonies per transformation were incubated anaerobically for 48 h at 30° C. in wells containing medium as used and described in J. Bacteriol. December 2000 vol. 182 no. 24 7007-7013 containing 240 g/L maltodextrin and 0.05% glucose at pH4.5 and 32° C. Results are in Table 2. From this first screening it was decided to select glucoamylases from *Trichoderma reesei, Talaromyces stipitatus, Piriformospora indica, Punctularia strigosozonata, Saccharomycopsis fibuligera*, and *Saccharomyces diastaticus*, since these were the only glucoamylases resulting in sufficient GA expression to facilitate anaerobic growth on a synthetic medium contain starch as sole C-source.

TABLE 2 micro-aerobic growth in microtiter plate

| | Native leader | Mat alpha leader |
|---|---|---|
| *Amorphotheca resinae* strain DAOM194228 | − | − |
| *Corynascus sepedonium* ATCC9787 | − | − |
| *Aspergillus niger* | − | − |
| *Trichoderma reesei* | + | + |
| *Botryotinia fuckeliana* BcDW1 | − | − |
| *Auricularia delicata* TFB-10046 SS5 | − | − |
| *Talaromyces stipitatus* ATCC 10500 | − | + |
| *Piriformospora indica* DSM 11827 | − | + |
| *Punctularia strigosozonata* HHB-11173 SS5 | + | + |
| *Saccharomycopsis fibuligera* | + | + |
| *Saccharomyces diastaticus* | + | + |

Next, colonies from the strains selected in the micro-aerobic MTP test were tested for growth on maltodextrin in a shake flask (SF) experiment under micro-aerobic conditions in Verduyn medium containing 240 g/L Maltodextrin+ 0.05% glucose+100× diluted Gibco™ Penicillin Streptomycin (10,000 U/mL) at pH4.5 and 30° C. for 72 h. The ability of degradation of maltodextrin was tested by NMR spectrometry by measuring the amount of α1→4 bonds, indicative of the amount of intact (i.e. not-converted) maltodextrin.

For the quantification of residual maltodextrin, 100 µl of the supernatant sample was transferred accurately into a suitable vial. Subsequently 100 µl internal standard solution, containing maleic acid (20 g/l), EDTA (40 g/l), DSS (4,4-dimethyl-4-silapentane-1-sulfonic acid) (0.5 g/L), and sodium hydroxide until pH 6.40, in $D_2O$ was added. This mixture was lyophilized and reconstituted in 600 µl $D_2O$.

1D $^1H$ NMR spectra of the clear solution were recorded on a Bruker Avance III HD spectrometer, operating at a proton frequency of 400 MHz, equipped with a prodigy probe, using a pulse program without water suppression (ZG), at a temperature of 295 K, with a 90 degree excitation pulse, acquisition time of 2.0 seconds and a relaxation delay of 40 seconds. The number of scans was set at 8, dummy scans were not used.

The analyte concentration [in gram per liter] was calculated based on the following signals (δ relative to DSS): maltodextrin: α-H1 polyglucose signal (m, 5.56-5.25 ppm), calculated as n=1, and a MW of 162 gram/mol. The signal used for the standard: maleic acid peak around 6.4 ppm (S, 2H). Results are in Table 3.

TABLE 3

Maltose degradation, judged by amount of α (1→4) bonds (arbitrary units)

| Glucoamylase | Leader | α (1→4) bonds | Maltose converted |
|---|---|---|---|
| Control (cells without glucoamylase) | — | 194.71 | 0 |
| *T. reesei* | Native | 81.55 | 58% |
| *Punctularia strigosozonata* | Native | 21.25 | 89% |
| *Saccharomycopsis fibuligera* | Native | 49.35 | 75% |
| *S. cerevisiae diastaticus* | Native | 136.95 | 30% |
| *T. reesei* | Sc_Mfalfa.sig | 71.1 | 63% |
| *Taloromyces stipitatus* | Sc_Mfalfa.sig | 144.32 | 26% |
| *Piriformospora indica* | Sc_Mfalfa.sig | 124.23 | 36% |
| *Punctularia strigosozonata* | Sc_Mfalfa.sig | 19.78 | 90% |
| *Saccharomycopsis fibuligera* | Sc_Mfalfa.sig | 34.68 | 82% |
| *S. cerevisiae diastaticus* | Sc_Mfalfa.sig | 120.25 | 38% |

It can be seen that with both native and *S. cerevisiae* alpha mating signal sequence the *Punctularia strigosozonata* GA gave the best performance.

Example 2

Four copies of the *Punctularia strigosozonata* glucoamylase (GA; SEQ ID NO: 17) containing the native leader sequence (SEQ ID NO: 37) were introduced into Ethanol Red, a commercial *Saccharomyces cerevisiae* yeast available from LeSaffre, using CRISPR-CAS9. In front of the open reading frame (ORF), the *S. cerevisiae* PGK1 promoter was placed, behind the ORF, the *S. cerevisiae* ENO1 terminator was placed. Besides the promoter-ORF-terminator sequence, the GA expression cassette contained on the 5' flank the 2.J connector sequence according to SEQ ID NO: 50 and on the 3' flank the 2.K connector sequence according to SEQ ID NO: 51.

To realize the correct targeted integration, flanks varying in length from 360 bp up to 520 bp containing the same connector sequences as the GA expression cassette, were amplified from the Ethanol Red yeast genome. The GA expression cassettes were targeted to integration loci, INT59 (target sequence according to SEQ ID NO: 52) and YPRcTAU3 (target sequence according to SEQ ID NO: 53) where both alleles were targeted, confirmed by diagnostic PCR. To obtain a marker-free strain, the cells were forced to lose their marker containing plasmids by growing several rounds on non-selective media. Finally, the marker-free strain was stored and named FS0209.

Corn mash (30% (w/w) solids) was prepared by mixing 333 g corn flour (Limagrain, Belgium) per kg mash, with 300 ml/kg thin stillage and 367 ml/kg demineralized water. The pH was adjusted to 5.5 with 2M KOH solution. Starch in the mixture was liquefied by adding 0.02 g/kg of a commercial alpha-amylase (Termamyl, Novozymes), and incubated for 4 hours at 80° C. in a rotary shaker. After liquefaction the pH was adjusted to 4.5 with 2M $H_2SO_4$ solution.

Ethanol red and FS0209 were pre-cultured by inoculating 200 ml YepH (20 g/l phytone peptone, 10 g/l yeast extract) supplemented with 2% w/v glucose, from a cryo-vial and incubated for 20 h in a 500 ml shake flask. To determine the inoculation volume of the yeast, the dry cell weight (DCW) content of the culture is determined by filtration and drying via a CEM-SMART microwave. A quantity of the preculture corresponding to the required inoculation size for the propagations were centrifuged (3 min, 4500×g), washed once with sterile demineralized water, centrifuged once more, resuspended in propagation medium and transferred to the propagation flasks.

Propagations were performed in 100 ml Erlenmeyer shake flasks with a foam stopper for 6 h at 32° C., 150 rpm, creating an aerobic environment. The propagation medium was diluted to a 70% solution, checked for pH 4.5 and was supplied with 1.25 g/l urea and antibiotics (neomycin and PenG). For ethanol red 0.088 g/l commercial amyloglucosidase enzyme (Spirizyme Excel, novozymes) was added.

Fermentations were performed in simultaneous saccharification fermentation (SSF) mode, using 500 ml schott bottles filled with 360 ml of corn mash in an AFM set up (Applikon, Schiedam, the Netherlands). The cornmash was used as such, with addition of 1 g/l urea and antibiotics, pH 4.5. Different concentrations of commercial amyloglucosidase enzyme (Spirizyme Excel, Novozymes) were added to the fermentation bottles. The inoculation of the fermenters was done by transferring 10% of the propagation medium to the fermenters, reaching 400 ml of volume. The pH was not controlled during the fermentations, while temperature was controlled at 32° C. Fermentation samples were taken throughout the run and different components were measured by HPLC analysis using a Dionex Ultimate 3000 HPLC system with column oven TCC-3400 and Autosampler WPS-3000 equipped with a guard column (Bio-Rad H cartridge) and an Aminex HPX-87H column (300×7.8 mm; Bio-Rad, Hercules, USA); elution took place at 65° C. with 5 mM $H_2SO_4$ at 0.55 ml/min; the eluate was monitored using a Refractive Index detector RefractoMax 521. $CO_2$ was measured online during the fermentation. Results are shown in Table 4.

TABLE 4

| | | Ethanol yields | | |
| --- | --- | --- | --- | --- |
| Strain | GA dose (g/kg) | 46 h | 53 h | 72 h |
| Ethanol red | 0.16 | 103.4 | 113.4 | 128.7 |
| Ethanol red | 0 | 15.5 | 15.7 | 16.0 |
| FS0209 | 0.08 | 113.8 | 121.9 | 130.4 |
| FS0209 | 0.04 | 122.3 | 125.7 | 136.5 |
| FS0209 | 0.02 | 107.4 | 113.2 | 122.9 |
| FS0209 | 0 | 119.2 | 122.1 | 123.9 |

The invention claimed is:

1. A recombinant yeast comprising:
a nucleotide sequence encoding a glucoamylase comprising an amino acid sequence that has at least 70% sequence identity to the amino acid sequence of SEQ ID NO:17.

2. The recombinant yeast according to claim 1 further comprising:
a nucleotide sequence coding for a glycerol dehydrogenase.

3. The recombinant yeast according to claim 1 further comprising:
a nucleotide sequence coding for a ribulose-1,5-biphosphate carboxylase oxygenase (EC 4.1.1.39, RuBisCO); and
a nucleotide sequence coding for a phosphoribulokinase (EC 2.7.1.19, PRK).

4. The recombinant yeast according to claim 1 further comprising a nucleotide sequence coding for a glycerol transporter.

5. The recombinant yeast according to claim 1 which comprises a deletion or disruption of one or more endogenous nucleotide sequences encoding a glycerol exporter.

6. The recombinant yeast according to claim 1 which comprises a deletion or disruption of one or more endogenous nucleotide sequences encoding a glycerol kinase (EC 2.7.1.30).

7. The recombinant yeast according to claim 1 which comprises a deletion or disruption of one or more endogenous nucleotide sequences encoding a glycerol-3-phosphate dehydrogenase (GPD1/2).

8. The recombinant yeast according to claim 1 which comprises a deletion or disruption of one or more endogenous nucleotide sequences encoding a glycerol 3-phosphate phosphohydrolase (GPP 1/2).

9. The recombinant yeast according to claim 1 which is a *Saccharomyces*, optionally *Saccharomyces cerevisiae*.

10. The recombinant yeast according to claim 1 further comprising one or more nucleotide sequences encoding a polypeptide comprising an amino acid sequence selected from the group consisting of SEQ ID NO:9, SEQ ID NO:10, functional homologues of SEQ ID NO:9, and functional homologues of SEQ ID NO:10.

11. A product comprising the recombinant yeast according to claim 1 for the preparation of ethanol and/or succinic acid.

12. A process for production of ethanol comprising:
fermenting a composition comprising a fermentable carbohydrate under anaerobic conditions in the presence of a recombinant yeast according to claim 1, wherein said fermentable carbohydrate optionally is selected from the group consisting of glucose, fructose, sucrose, maltose, xylose, arabinose, galactose, and mannose; and
recovering ethanol.

13. The process according to claim 12 wherein fermentable carbohydrate is obtained from starch, lignocellulose, and/or pectin.

14. The process according to claim 12 wherein said composition further comprises undissociated acetic acid in an amount of 10 mM or less.

15. The process according to claim 12 wherein said composition further comprises undissociated acetic acid in an amount of between 50 μM and 10 mM.

16. The process according to claim 12 which further comprises adding glucoamylase at a concentration of 0.05 g/L or less.

* * * * *